US008877739B2

(12) United States Patent (10) Patent No.: US 8,877,739 B2
Yasuda et al. (45) Date of Patent: Nov. 4, 2014

(54) PROPHYLACTIC AGENT OR THERAPEUTIC AGENT FOR DIABETES OR OBESITY

(71) Applicant: Ajinomoto Co., Inc., Tokyo (JP)

(72) Inventors: Reiko Yasuda, Kawasaki (JP); Yuzuru Eto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/630,562

(22) Filed: Sep. 28, 2012

(65) Prior Publication Data

US 2013/0102570 A1 Apr. 25, 2013

Related U.S. Application Data

(63) Continuation of application No. PCT/JP2011/058855, filed on Mar. 31, 2011.

(30) Foreign Application Priority Data

Apr. 2, 2010 (JP) .................................. 2010-085741

(51) Int. Cl.
*A61K 31/662* (2006.01)

(52) U.S. Cl.
USPC .......................................................... 514/119

(58) Field of Classification Search
None
See application file for complete search history.

(56) References Cited

U.S. PATENT DOCUMENTS

| | | | | |
|---|---|---|---|---|
| 4,177,109 | A * | 12/1979 | Tohyama et al. ............... | 435/24 |
| 2007/0065839 | A1 * | 3/2007 | Attie et al. ........................ | 435/6 |
| 2007/0281906 | A1 * | 12/2007 | Dalton et al. .................... | 514/80 |
| 2011/0028394 | A1 | 2/2011 | Karim et al. | |
| 2011/0046046 | A1 | 2/2011 | Hara et al. | |
| 2011/0251418 | A1 | 10/2011 | Sugiki et al. | |
| 2012/0101039 | A1 | 4/2012 | Fenscholdt et al. | |
| 2012/0122784 | A1 | 5/2012 | Norremark et al. | |
| 2012/0129926 | A1 | 5/2012 | Norremark | |
| 2013/0012432 | A1 * | 1/2013 | Conde-Frieboes et al. .... | 514/4.9 |

FOREIGN PATENT DOCUMENTS

| | | |
|---|---|---|
| JP | 55-036428 | 3/1980 |
| JP | 06-172287 | 6/1994 |
| WO | 2007/055388 | 5/2007 |
| WO | 2007/055393 | 5/2007 |
| WO | 2009/107660 | 9/2009 |
| WO | 2010/038895 | 4/2010 |
| WO | 2010/136035 | 12/2010 |
| WO | 2010/136036 | 12/2010 |
| WO | 2010/136037 | 12/2010 |
| WO | 2011/014707 | 2/2011 |
| WO | 2010/108724 | 9/2011 |
| WO | 2011/108690 | 9/2011 |

OTHER PUBLICATIONS

Shah, Unmesh, and Timothy J. Kowalski, GPR 119 Agonists for the Potential Treatment of Type 2 Diabetes and Related Metabolic Disorders, in Vitamins and Hormones, vol. 84, @2010 Elsevier, Inc., p. 415.*
Choquet, H. Molecular Basis of Obesity: Current Status and Future Prospects, in Current Genomics, vol. 12, p. 154-168. Published by Bentham Science Publishers, LtD.*
Boekelheide, et al. "Melanocytotoxicity and the Mechanism of Activation of gamma-L-Glutaminyl-4-hydroxybenzene", The Journal of Investigative Dermatology, 75: 322-327, 1980).*
I-Lin Lu, et al., "Glutamic acid analogues as potent dipeptidyl peptidase IV and 8 inhibitors," Bioorganic Medicinal Letters, 15, (2005), p. 3271-3275.*
Helene Choquet Choquet, Helene University of California, San Francisco, Ernest Gallo Clinic and Research Center, Department of Neurology Article or Chapter Title: Molecular Basis of Obesity: Current Status and Future Prospects Helene, Choquet, Molecular Basis of Obesity: Current Status Current genomics, 2011, 12, 154-168.*
U.S. Appl. No. 13/624,254, filed Sep. 21, 2012, Sugiki, et al.
U.S. Appl. No. 13/601,141, filed Aug. 31, 2012, Yasuda, et al.
A. Weller et al., "Endogenous Cholecystokinin Reduces Feeding in Young Rats", Science, vol. 247, (1990) pp. 1589-1591.
T. Woltman et al., "Role of cholecystokinin in the anorexia produced by duodenal delivery of peptone in rats", American Journal of Physiology, vol. 276 (1999) pp. R1701-R1709.
L. Rossetti et al., "Physiological Role of Cholecystokinin in Meal-Induced Insulin Secretion in Conscious Rats", Diabetes, vol. 36 (1987) pp. 1212-1215.
R. Rushakoff et al., "Physiological Concentrations of Cholecystokinin Stimulate Amino Acid-Induced Insulin Release in Humans", Journal of Clinical Endocrinology Metabolism , vol. 65, No. 3 (1987) pp. 395-401.
Szasz et al., "Reaction-Rate Method for γ-Glutamyltransferase Activity in Serum", Clinical Chemistry, vol. 22, No. 12, (1976) pp. 2051-2055.
R. Lloyd et al., "α- and γ-Glutamyl Derivatives of Aminobenzoic Acids", Journal of Medicinal Chemistry, vol. 8, No. 3 (1965) pp. 398-400.
S. Bashir et al., "Parameterising matrix-assisted laser desorption/ionisation (MALDI): strategy for matrix-analyte selection and effect of radical co-additives on analyte peak intensities", Analytica Chimica Acta, vol. 519, No. 2 (2004) pp. 181-187.
M. Wang et al., "Activation of Family C G-protein-coupled Receptors by the Tripeptide Glutathione", Journal of Biological Chemistry, vol. 281, No. 13, (2006) pp. 8864-8870.
T. Ohsu et al., "Involvement of the Calcium-sensing Receptor in Human Taste Perception" Journal of Biological Chemistry, vol. 285, No. 2, (2010) pp. 1016-1022.
A. Rosowsky et al., "Structural Analogues of $_L$-Glutamic Acid γ-(4-Hydroxyanilide and γ-(3,4-Dihydroxyanilide) as Potential Agents against Melanoma", Journal of Medicinal Chemistry, vol. 22, No. 9 (1979) pp. 1034-1037.
J. Keillor et al., "Pre-steady-state kinetic studies of rat kidney γ-glutamyl transpeptidase confirm its ping-pong mechanism", Journal of Physical Organic Chemistry, vol. 17, (2004) pp. 529-536.
International Search Report issued on Jun. 28, 2011 in PCT/JP2011/058855 filed Mar. 31, 2011.

(Continued)

*Primary Examiner* — San-Ming Hui
*Assistant Examiner* — Jeanmarie Calvillo
(74) *Attorney, Agent, or Firm* — Oblon, Spivak, McClelland, Maier & Neustadt, L.L.P.

(57) ABSTRACT

A medicament having an excellent CaSR agonist action which enables the prevention or treatment of diabetes or obesity is provided by a composition comprising the compound represented by general formula (I) as defined, or a salt thereof.

10 Claims, No Drawings

(56) References Cited

OTHER PUBLICATIONS

Notification of Translation of International Report on Patentability mailed Nov. 22, 2012 issued in PCT/JP2011/058855 filed Mar. 31, 2011.
International Preliminary Report on Patentability issued Nov. 13, 2012 issued in PCT/JP2011/058855 filed on Mar. 31, 2011.
Written Opinion mailed Jun. 28, 2011 issued in PCT/JP2011/058855 filed on Mar. 31, 2011.
Extended European Search Report issued Mar. 27, 2014, in European Patent Application No. 11765999.5.
Elizabeth Gray, et al.; "Activation of the extracellular calcium-sensing receptor initiates insulin secretion from human islets of Langerhans: involvement of protein kinases"; Journal of Endocrinology (2006) 190, pp. 703-710.
K. A. Sobiech, et al.; "Effect of Intestinal γ-glutamyl Transferase Inhibitor on the Amount of γ-glutamyl Metabolites in Mouse"; Folia Histochemica et Cytochemica; vol. 17 (1979) No. 2 pp. 147-152.

* cited by examiner

PROPHYLACTIC AGENT OR THERAPEUTIC AGENT FOR DIABETES OR OBESITY

CROSS-REFERENCE TO RELATED APPLICATIONS

The present application is a continuation of and claims the benefits of priority to International Application PCT/JP2011/058855, filed Mar. 31, 2011, which claims the benefits of priority to Japanese Application No. 2010-085741, filed Apr. 2, 2010.

TECHNICAL FIELD

The present invention relates to a glutamic acid derivative having a CaSR agonist activity or a pharmaceutically acceptable salt thereof as well as a preventive or therapeutic agent for diabetes or obesity comprising as an active ingredient the derivative or a pharmaceutically acceptable salt thereof.

BACKGROUND ART

Energy metabolism in the body is controlled by insulin produced in pancreatic β cells. Insulin acts on peripheral tissues or cells and plays an important role in controlling blood sugar levels by promoting the assimilation of sugar from the blood. However, when a high caloric meal is taken continuously and insulin sensitivity in cells decreases, elevation of blood glucose levels and oversecretion of insulin proceed simultaneously. As a result, pancreatic β cells are exhausted to become dysfunctional and develop diabetes or obesity.

Insulin secretion is regulated by various hormones. In particular, glucagon-like peptide-1 (GLP-1) that is produced and secreted in the gastrointestinal tract is considered important. GLP-1 is a peptide hormone with a molecular weight of approximately 4,000 and produced mainly in the L-cells of the small intestine. It has been revealed that GLP-1 has activities of promoting insulin secretion from β cells, suppressing gastric peristalsis and digestive absorption, suppressing appetite, bulimia or the like and is thus effective for the treatment or prevention of diabetes or obesity. It is known that GLP-1 production capacity decreases in diabetes and obesity. If GLP-1 production can be promoted in the clinical entities of these diseases, it is expected to lead to the treatment and prevention of diabetes or obesity The production of GLP-1 in the L cells is promoted by uptake of a variety of nutrition including carbohydrates, lipids, proteins, etc. However, compounds such as specific peptide components, etc. are rarely utilized as a GLP-1 secretion promoter.

Cholecystokinin (CCK) is a peptide hormone with a molecular weight of approximately 4,000, which is produced mainly in the L-cells of the duodenum and the small intestine, and promotes the secretion of bile and the secretion of pancreatic digestive juice. Physiological effects of CCK that are particularly noteworthy involve an activity of suppressing gastric emptying of food, an activity of promoting pancreatic enzyme secretion and an anorexigenic effect on food intake by a sense of satiation (Non-Patent Documents 1 and 2). In addition, there is also known an activity of promoting the secretion of insulin that is a glucoregulatory hormone (Non-Patent Documents 3 and 4). CCK has these activities or effects and is considered to be promising for the treatment or prevention of lifestyle-related diseases such as diabetes, obesity, pancreatitis, etc.

GLP-1 and CCK are peptides and are to be administered intravascularly by injecting GLP-1 and CCK, etc. to make them available for therapy, but such is not realistic due to the complicated daily administration and considerable expense. On the other hand, it is considered to use such a mechanism that endogenous GLP-1 and CCK are secreted from GLP-1 and CCK-producing cells in the small intestinal mucosa by proteins, peptides, amino acids, fatty acids, etc., of dietary constituents. That is, it has been desired to develop compounds or food materials having the GLP-1 and CCK secretion promoting activity.

On the other hand, a calcium sensing receptor (CaSR), which is also called a calcium receptor, transduces the receptor signals to regulate various in vivo functions. Thus, there is a possibility that substances having a CaSR agonist activity are useful for treating or preventing various diseases and also useful as kokumi-imparting agents. Patent Document 1 discloses a screening method for a kokumi-imparting substance and a kokumi-imparting agent containing a kokumi-imparting substance obtainable by the screening method. It has been found that a variety of low molecular peptides possess the CaSR agonist activity, and described that based on this finding, it has become possible to provide a kokumi-imparting agent capable of imparting "kokumi taste," i.e., the taste that cannot be expressed only with five basic tastes of sweet, salty, sour, bitter and umami tastes, and the taste that enhances marginal tastes of the basic tastes described above, such as thickness, growth (mouthfullness), continuity and harmony.

Furthermore, it has been known from old that γ-glutamylanilide derivatives act as the substrate for γ-glutamyltransferase and can be used for enzyme activity measurements (Non-Patent Document 5, Patent Document 2). However, no publication discloses any relation to "calcium sensing receptor (CaSR) or G protein-coupled receptor," "diabetes or obesity," "promotion of GLP-1 secretion," "promotion of CCK secretion," "suppression of gastric emptying," etc., which are characteristic features of the present invention.

On the other hand, cinacalcet or synthetic low molecular compounds analogous thereto as well as γ-glutamylpeptide derivatives including glutathione are known as compounds for activating CaSR (Patent Document 4, Non-Patent Documents 8 and 9). Among them, a part of the compounds are also known to have use as therapeutic agents for diabetes or obesity (Patent Document 5). However, these compounds are structurally different from the glutamic acid derivative of the present invention.

Also in some known compounds among 3-sulfonic acids, 3-carboxylic acids and 3-nitro derivatives, which are particularly preferred in the present invention, most of their utilities are focused on substrates in enzymatic activity measurements of γ-glutamyltransferase; antibacterial agents or antiallergic agents (Non-Patent Document 6 and Patent Document 3) and analysis reagents for mass spectrometry (Non-Patent Document 7) are only a few other known uses.

It is therefore expected to explore compounds with numerous variations having the CaSR agonist activity and provide more excellent preventive or therapeutic agents for diabetes or obesity.

PRIOR ART DOCUMENTS

Patent Documents

[Patent Document 1] WO2007/055393A1 Pamphlet
[Patent Document 2] WO2007/055393A1 Pamphlet
[Patent Document 3] JPA 06-172287
[Patent Document 4] WO2007/055388A2 Pamphlet

[Patent Document 5] WO2009/107660 Pamphlet

Non-Patent Documents

[Non-Patent Document 1] Science, vol. 247, p. 1589-1591, 1990
[Non-Patent Document 2] American Journal of Physiology, vol. 276, R1701-R1709, 1999
[Non-Patent Document 3] Diabetes, vol. 36, p. 1212-1215, 1987
[Non-Patent Document 4] Journal of Clinical Endocrinological Metabolism, vol. 65, p. 395-401, 1987
[Non-Patent Document 5] Clinical Chemistry, 22, 2051 (1976)
[Non-Patent Document 6] Journal of Medicinal Chemistry (1965), 8(3), 398-400
[Non-Patent Document 7] Analytica Chimica Acta (2004), 519(2), 181-187
[Non-Patent Document 8] Journal of Biological Chemistry (2006), 281(13), 8864-70
[Non-Patent Document 9] Journal of Biological Chemistry, (2010), 285 (2), 1016-22

DISCLOSURE OF THE INVENTION

Problems to be Solved by the Invention

The present invention aims at investigating compounds with numerous variations having the CaSR agonist activity and providing preventive or therapeutic agents for diabetes or obesity comprising such compounds.

Means for Solving the Problems

As a result of the investigations of compounds having the CaSR agonist activity, surprisingly, the inventors have found that various γ-glutamic acid derivatives and analogues thereof (hereinafter referred to as the "glutamic acid derivative") have the excellent CaSR agonist activity. They have also found that the glutamic acid derivative having the CaSR agonist activity or pharmaceutically acceptable salts thereof can be a useful preventive or therapeutic agent for diabetes or obesity. The present invention has thus been accomplished.

That is, the present invention provides a preventive or therapeutic agent for diabetes or obesity, comprising the following glutamic acid derivative or a pharmaceutically acceptable salt thereof. The present invention provides the following features.

[1] A preventive or therapeutic agent for diabetes or obesity, comprising a glutamic acid derivative represented by general formula (I) below:

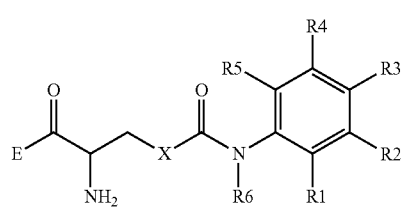

(I)

(wherein $R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), or a $C_{1-6}$ mono- or dialkylamino group which may have a substituent(s), sulfo group, or a group below:

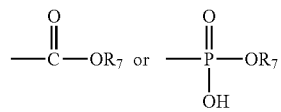

provided that either one of $R^1$, $R^2$ or $R^3$ is a group selected from nitro group, sulfo group or a group:

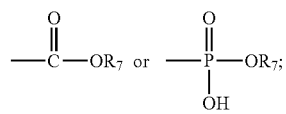

$R^6$ is hydrogen atom, hydroxyl group or a $C_{1-6}$ alkyl group which may have a substituent(s);
$R^7$ is hydrogen atom or a $C_{1-6}$ alkyl group which may have a substituent(s);
X is methylene group or oxygen atom; and,
E is hydroxyl group, a $C_{1-6}$ alkoxyl group which may have a substituent(s), a mercapto group which may have a substituent(s), or a group below:

 (IIa)

 (IIb)

(wherein: Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), $E^2$ is hydrogen atom or a $C_{1-6}$ alkyl group, and Z and $E^1$ may be combined together to form a ring);
or a pharmaceutically acceptable salt thereof
[1-2] The preventive or therapeutic agent for diabetes or obesity, according to [1], wherein in general formula (I):
$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s) or a $C_{1-6}$ mono- or dialkylamino group which may have a substituent(s), sulfo group or a group:

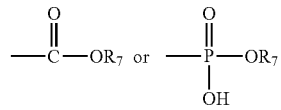

provided that either one of $R^1$, $R^2$ and $R^3$ is a group selected from nitro group, sulfo group and a group:

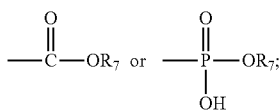

$R^6$ is hydrogen atom, hydroxyl group or a $C_{1-6}$ alkyl group which may have a substituent(s);

$R^7$ is hydrogen atom or a $C_{1-6}$ alkyl group which may have a substituent(s);

X is methylene group or oxygen atom; and,

E is selected from hydroxyl group, a $C_{1-6}$ alkoxy group which may have a substituent(s), a mercapto group which may have a substituent(s), or a group below:

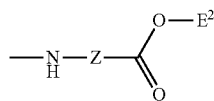

(IIb)

(wherein Z is a divalent $C_{1-6}$ hydrocarbon group which may have a substituent(s) and $E^2$ is hydrogen atom or a $C_{1-6}$ alkyl group).

[2] The preventive or therapeutic agent for diabetes or obesity according to [1] or [1-2] above, wherein; in general formula (I):

$R^1$, $R^3$, $R^4$ and $R^5$ each independently represents a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), and a $C_{1-6}$ mono- or dialkylamino group which may have a substituent(s);

$R^2$ is a group selected from nitro group, sulfo group or a group:

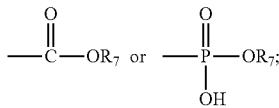

$R^6$ and $R^7$ each independently represents hydrogen atom or a $C_{1-6}$ alkyl group which may have a substituent(s); and, X is methylene group or oxygen atom.

[3] The preventive or therapeutic agent for diabetes or obesity, according to [1] to [2], wherein, in general formula (I):

$R^1$, $R^3$, $R^4$ and $R^5$ each independently represents a group selected from hydrogen atom, a halogeno group, hydroxyl group, nitro group, amino group, a $C_{1-3}$ alkyl group which may have a substituent(s), a $C_{1-3}$ alkoxy group which may have a substituent(s), and a $C_{1-3}$ mono- or dialkylamino group which may have a substituent(s);

$R^2$ is a group selected from nitro group, sulfo group or a group:

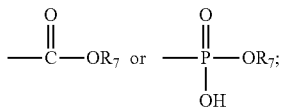

and, $R^6$ and $R^7$ each independently represents hydrogen atom or methyl group.

[4] The preventive or therapeutic agent for diabetes or obesity, according to any one of [1] to [3], wherein, in general formula (I):

$R^1$, $R^3$, $R^4$ and $R^5$ each independently represents a group selected from hydrogen atom, chloro or bromo group, hydroxyl group, nitro group, amino group, methyl group or methoxy group;

$R^2$ is a group selected from nitro group, sulfo group and a group below:

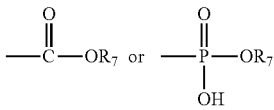

$R^6$ is hydrogen atom or methyl group;

$R^7$ is hydrogen atom; and,

X is methylene group.

[5] The preventive or therapeutic agent for diabetes or obesity, according to any one of [1] to [4], wherein, in general formula (I), $R^2$ is sulfo group, a carboxylic acid group or a phosphonic acid group.

[6] The preventive or therapeutic agent for diabetes or obesity, according to any one of [1] to [5], wherein, in general formula (I), E is hydroxyl group or a $C_{1-6}$ alkoxy group which may have a substituent(s).

[7] The preventive or therapeutic agent for diabetes or obesity, according to any one of [1] to [6], wherein, in general formula (I):

E is a $C_{1-6}$ alkoxy group or a group below:

-O-Z-$E^1$ (IIa)

wherein, in formula (IIa), Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), and Z and $E^1$ may be combined together to form a ring.

Effects of the Invention

According to the present invention, various compounds having an excellent CaSR agonist activity can be provided, and preventive or therapeutic agents for diabetes or obesity can also be provided.

BEST MODES FOR CARRYING OUT THE INVENTION

Hereinafter the present invention is described in detail.

As used herein, the "$C_{1-6}$ alkyl group" is a monovalent group derived by removing one optional hydrogen atom from a straight or branched aliphatic hydrocarbon having 1 to 6 carbon atoms. Specific examples include groups such as methyl, ethyl, isopropyl, butyl, n-butyl, isobutyl, sec-butyl, t-butyl, pentyl, isopentyl, 2,3-dimethylpropyl, hexyl, etc., and preferably, a $C_{1-3}$ alkyl group.

The "$C_{1-6}$ alkoxy group" is intended to mean a $C_{1-6}$ alkyl-O—. Specific examples include groups such as methoxy, ethoxy, 1-propoxy, 2-propoxy, n-butoxy, i-butoxy, sec-butoxy, t-butoxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, etc., and preferably, a $C_{1-3}$ alkoxy group.

The "halogeno group" includes fluorine atom, chlorine atom, fluorine atom and iodine atom.

The "mono- or di-$C_{1-6}$ alkylamino group" means an amino group wherein one or two hydrogen atoms are substituted with the $C_{1-6}$ alkyl group described above. Examples include groups such as methylamino, dimethylamino, ethylamino, diethylamino, etc., and preferably, a mono- or di-$C_{1-3}$ alkylamino group.

The "$C_{1-6}$ acyloxy group" is intended to mean a group shown by $C_{1-6}$ alkyl-C(O)—O—, $C_{3-6}$ cycloalkyl-C(O)—O— or phenyl-C(O)—O—. As used herein, the $C_{3-6}$ cycloalkyl group includes groups such as cyclopropyl, cyclopentyl, cyclohexyl, etc. The $C_{1-6}$ acyloxy group includes groups such as acetyloxy, propionyloxy, cyclohexylcarbonyloxy, benzoyloxy, etc., preferably, a $C_{1-6}$ alkyl-C(O)—O— and more preferably, a $C_{1-3}$ alkyl-C(O)—O— group.

The "$C_{1-6}$ alkoxycarbonyl group" is intended to mean a group shown by $C_{1-6}$ alkyl-O—C(O)— and includes groups such as methoxycarbonyl, ethoxycarbonyl, etc., and preferably, a $C_{1-3}$ alkoxycarbonyl group.

The "$C_{1-6}$ alkoxycarbonyloxy group" is intended to mean a group shown by $C_{1-6}$ alkyl-O—C(O)—O—, and includes groups such as methoxycarbonyloxy, ethoxycarbonyloxy, etc., and preferably, a $C_{1-3}$ alkoxycarbonyloxy group.

The "aryl group" is intended to mean an aromatic hydrocarbon cyclic group such as phenyl, naphthyl, etc., and preferably, phenyl group.

The "heteroaryl group" is a 5-membered to 10-membered aromatic heterocyclic group containing 1, 2 or 3 hetero atoms selected from N, S and O. Specific examples of the aromatic hetero ring include groups such as pyridine, pyridazine, pyrazine, pyrimidine, thiazole, isothiazole, oxazole, isoxazole, oxadiazole, pyrazole, imidazole, furan, thiophene, pyrrole, etc. Preferred are groups from pyridine, imidazole, thiophene, oxadiazole, indole, etc. and preferably, a 5-membered to 6-membered aromatic hetero ring and specific examples are groups from pyridine, pyrimidine, etc.

The "divalent $C_{1-6}$ hydrocarbon group" is intended to mean a straight or branched group having 1 to 6 carbon atoms, derived by removing two optional hydrogen atoms from an aliphatic hydrocarbon, which may optionally contain 1 or more double bonds or triple bonds. Specific examples include groups such as methylene, ethane-1,1-diyl, vinylene, ethynylene, propargyl, etc.

When E is represented by formula (IIa), the "ring" in E which is formed by combining Z and $E^1$ together is intended to mean a saturated or unsaturated 5- or 6-membered ring, which contains Z-$E^1$ as a part of the ring and may further optionally contain 1 to 3 hetero atoms selected from nitrogen atom, oxygen atom and sulfur atom as a ring constituent atom(s) and may be further condensed with a benzene ring. The ring is preferably a saturated or unsaturated 5- or 6-membered ring, which may optionally contain 1 to 3 oxygen atoms as a ring constituent atom. When Z and $E^1$ are combined together to form a ring, specific examples of E include the following groups.

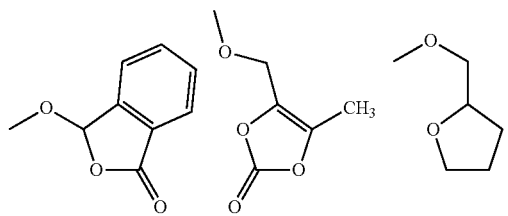

The group shown by E-CO— described above can also function as a carboxyl group modified to form a prodrug that is converted into a carboxyl group in vivo, as described in, e.g., Prog. Med. 5: 2157-2161 (1985), IYAKUHIN-NO-KAIHATSU (Development of Drugs) (published by Hirokawa Shoten in 1990), volume 7, Bunshi Sekkei (Molecule Design), p. 163-198, or SAISHIN SOYAKU-KAGAKU (Recent Innovative Drug Chemistry) (published by Technomics, Inc. in 1999), last volume, p. 271-298.

In the glutamic acid derivative in general formula (I) described above, which is contained in the preventive or therapeutic agent for diabetes or obesity of the present invention, $R^1$, $R^2$, $R^3$, $R^4$ and $R^5$ each independently is preferably a group selected from hydrogen atom, a halogeno group, hydroxyl group, nitro group, amino group, an alkyl group having 1 to 3 carbon atoms which may have a substituent(s), an alkoxy group having 1 to 3 carbon atoms which may have a substituent(s), or a mono- or dialkylamino group having 1 to 3 carbon atoms which may have a substituent(s). Also in $R^1$, $R^2$, $R^3$, $R^4$ and $R^5$, any one of $R^1$, $R^2$ and $R^3$ is preferably a group selected from sulfo group or a group.

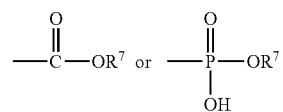

On the other hand, $R^1$, $R^3$, $R^4$ and $R^5$ each independently is preferably a group selected from hydrogen atom, a halogeno group, hydroxyl group, nitro group, amino group, a $C_{1-3}$ alkyl group which may have a substituent(s), a $C_{1-3}$ alkoxy group which may have a substituent(s) and a mono- or di-$C_{1-3}$ alkylamino group which may have a substituent(s). More preferably, $R^1$, $R^3$, $R^4$ and $R^5$ each independently is a group selected from hydrogen atom, chloro or bromo group, hydroxyl group, nitro group, amino group, methyl group and methoxy group.

In general formula (I) described above, which is contained in the preventive or therapeutic agent for diabetes or obesity of the present invention, $R^2$ is preferably sulfo group, a carboxylic acid group or a phosphonic acid group.

Alternatively, either one of $R^1$ and $R^3$ may be sulfo group and in this case, it is also preferred that $R^4$ is a halogeno group.

In general formula (I) above, which is contained in the preventive or therapeutic agent for diabetes or obesity of the present invention, $R^6$ and $R^7$ each independently is preferably a hydrogen atom or methyl group. More preferably, $R^6$ is hydrogen atom or methyl group and $R^7$ is hydrogen atom. It is also preferred that $R^6$ is hydroxyl group.

In general formula (I) above, which is contained in the preventive or therapeutic agent for diabetes or obesity of the present invention, X is preferably methylene group or oxygen atom.

In general formula (I) above, which is contained in the preventive or therapeutic agent for diabetes or obesity of the present invention, E is preferably hydroxyl group or a $C_{1-6}$ alkoxyl group which may have a substituent(s), more preferably, hydroxyl group or a $C_{1-6}$ alkoxy group, and particularly preferably, hydroxyl group or a $C_{1-3}$ alkoxy group.

In the glutamic acid derivative represented by general formula (I) above or a pharmaceutically acceptable salt thereof, which is contained in the preventive or therapeutic agent for diabetes or obesity of the present invention, either one of $R^1$, $R^2$ or $R^3$ is preferably sulfo group, a carboxylic acid group or a phosphonic acid group. Inter alia, $R^2$ is preferably sulfo group, a carboxylic acid group or a phosphonic acid group, and particularly preferably, sulfo group.

Particularly when $R^2$ is sulfo group in general formula (I) above, it is preferred that $R^1$ is hydrogen atom or hydroxyl group, $R^3$ is hydrogen atom, chloro group, hydroxyl group, methyl group or methoxy group, $R^4$ is hydrogen atom, chloro group or nitro group, $R^5$ is hydrogen atom, hydroxyl group, methyl group or methoxy group, $R^6$ is hydrogen atom or methyl group, and X is methylene group or oxygen atom. When $R^2$ is sulfo group in general formula (I) above, it is most preferred that $R^1$ is hydrogen atom or hydroxyl group, $R^3$ is hydrogen atom, chloro group or methyl group, $R^4$ is hydrogen atom or chloro group, $R^5$ is hydrogen atom, hydroxyl group or methyl group, $R^6$ is hydrogen atom, and X is methylene group or oxygen atom.

In the glutamic acid derivative represented by general formula (I) above or its pharmaceutically acceptable salt which is contained in the preventive or therapeutic agent for diabetes or obesity, particularly when $R^2$ is a carboxylic acid group in general formula (I) above, $R^1$ is hydrogen atom or hydroxyl group, $R^3$ is hydrogen atom, $R^4$ is hydrogen atom or bromo group, $R^5$ is hydrogen atom, $R^6$ is hydrogen atom and X is methylene group; it is most preferred that X is methylene group.

In the glutamic acid derivative represented by general formula (I) above or its pharmaceutically acceptable salt, which is contained in the preventive or therapeutic agent for diabetes or obesity, particularly when $R^2$ in general formula (I) above is —PO(OCH$_3$)OH group or —PO(OH)$_2$ group, it is most preferred that $R^1$ is hydrogen atom, $R^3$ is hydrogen atom, $R^4$ is hydrogen atom, $R^5$ is hydrogen atom, $R^6$ is hydrogen atom and X is methylene group or oxygen atom.

In the glutamic acid derivative represented by general formula (I) above or its pharmaceutically acceptable salt, which is contained in the preventive or therapeutic agent for diabetes or obesity, particularly when $R^2$ in general formula (I) above is nitro group, it is most preferred that $R^1$ is hydrogen atom, $R^3$ is hydrogen atom, $R^4$ is hydrogen atom, $R^5$ is hydrogen atom, $R^6$ is hydrogen atom and X is methylene group.

Also, in the glutamic acid derivative represented by general formula (I) above, particularly preferred are the compounds described in EXAMPLES. Inter alia, Compound Nos. 1, 7, 10, 21, 22, 24, 32, 33, 34, 35 and 37 are preferred. In particular, Compound Nos. 7, 10, 21, 22, 24, 32, 33, 34, 35 and 37 are preferred.

The alkyl group, alkoxy group and mono- or dialkylamino group in general formula (I) above each independently may have a substituent(s), and examples of the substituent(s) include, but not limited thereto, a halogen, hydroxy group, an alkoxy group, amino group, a mono- or dialkylamino group, carboxyl group and sulfo group. The alkoxy group and the mono- or dialkylamino group used as the substituent(s) are preferably a lower alkoxy group and a lower mono- or dialkylamino group, respectively. As used herein, the term lower is intended to mean 1 to 3 carbon atoms in total in the substituents.

The glutamic acid derivative represented by general formula (I) above, which is contained in the preventive or therapeutic agent for diabetes or obesity of the present invention, may be in the form of pharmaceutically acceptable salts thereof. The pharmaceutically acceptable salts of the glutamic acid derivative of the present invention represented by general formula (I) above includes edible salts, and examples of the salts with acidic groups such as a carboxyl group, sulfo group, etc. in the formula are ammonium salts, salts with alkali metals such as sodium, potassium, etc., salts with alkaline earth metals such as calcium, magnesium, etc., aluminum salts, zinc salts, salts with organic amines such as triethylamine, ethanolamine, morpholine, pyrrolidine, piperidine, piperazine, dicyclohexylamine, etc., and salts with basic amino acids such as arginine, lysine, etc. When a basic group(s) exists in the formula, the salts with such basic groups include salts with inorganic acids such as hydrochloric acid, sulfuric acid, phosphoric acid, nitric acid, hydrobromic acid, etc., salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, etc., and salts with organic sulfonic acids such as methanesulfonic acid, benzenesulfonic acid and p-toluenesulfonic acid.

As used herein, "CaSR" is intended to mean a calcium sensing receptor, and belongs to the class C family of seven transmembrane receptors. CaSR is also called a calcium receptor. As used herein, the term "CaSR agonist" is intended to mean a compound binding to the above CaSR to activate CaSR, and the term "CaSR agonist agent" is intended to mean an agent or substance binding to the above CaSR to activate CaSR. As used herein, the term "activate CaSR" is intended to mean that a ligand binds to CaSR thereby to activate guanine nucleotide-binding proteins and transmit signals. The behavior that a compound binds to CaSR to activate CaSR is termed "CaSR agonist activity"

A preferred example of the CaSR described above includes human CaSR encoded by human CaSR gene which is registered as GenBank Accession No. NM_000388. Meanwhile, CaSR is not limited to the protein encoded by the gene of the sequence described above and may be proteins encoded by the gene having 60% or more, preferably 80% or more, and more preferably 90% or more homology, to the sequence described above, as long as CaSR encodes proteins having the CaSR function. The CaSR function can be examined by expressing these genes in cells and measuring changes of current and changes of intracellular calcium ion level upon calcium addition.

The origin of CaSR described above is not particularly limited, and examples include any animal-derived CaSR such as those of mouse, rat, canine, etc., in addition to the human CaSR.

As described above, the CaSR activity can be confirmed by using living cells expressing CaSR or its fragments, cell membranes expressing CaSR or its fragments, an in vitro system containing proteins of CaSR or its fragments.

An example using living cells is given below but the activity confirmation is not limited thereto.

CaSR is expressed in culture cells of *Xenopus oocytes*, hamster ovary cells, human embryonic kidney cells, etc. The expression is enabled by cloning a CaSR gene to a plasmid bearing a foreign gene, and then introducing cRNA in the plasmid state or cRNA generated from the template. The reaction can be detected by electrophysiological means, or using a fluorescence indicator for detecting an increase of intracellular calcium.

The expression of CaSR is confirmed initially by a response to calcium or a specific activator.

Oocytes wherein the intracellular current was observed or culture cells wherein fluorescence from a fluorescence indicator was observed are used for calcium of approximately 5 mM concentration. Concentration dependence is monitored by varying the concentration of calcium. Next, a test substance is prepared to become 1 µM to 1 mM, which is added to oocytes or culture cells. Then, the CaSR activity is determined in the presence of the test substance to determine the CaSR agonist activity of the test substance described above.

CaSR is expressed in various tissues and plays various physiological activities. For example, it is shown that CaSR promotes the secretion of GLP-1 and CCK from STC-1 cells and GLUTag cells in the intestinal tract by peptides or low molecular compounds that activate the calcium receptor (WO 2009/11221). For this reason, the compounds having the CaSR agonist action are shown to be useful as preventive or therapeutic agents for diabetes (The Journal of Biological Chemistry, 1999, vol. 274, p. 20561-20568 and The Journal of Biological Chemistry, 2000, vol. 275, p. 18777-18784) or obesity. In fact, the compound of the present invention is confirmed to have the activity of promoting the secretion of GLP-1 and CCK (cf., EXPERIMENTAL EXAMPLE later described) and thus can be used as the preventive or therapeutic agent for diabetes or obesity. The compound of the present invention can also be used as a secretion promoter of GLP-1 or CCK. Moreover, the compound of the present invention can be used as a gastric emptying inhibitor and also used as an anorectic agent based on the gastric emptying inhibitory activity The preventive or therapeutic agent for diabetes or obesity of the present invention may further contain all glutamic acid derivatives included in the glutamic acid derivative of the present invention represented by general formula (I) or pharmaceutically acceptable salts thereof, alone or in combination of 2 or 3 more, and may further contain all solid or liquid carriers or additives that are pharmaceutically, physiologically and empirically acceptable and also acceptable as a food product.

The method of applying the preventive or therapeutic agent for diabetes or obesity of the present invention is not particularly limited, and any invasive or non-invasive administration such as oral administration and injection is applicable. Suppository or percutaneous administration is also applicable. The active ingredient may be formulated and administered in the form of a conventional pharmaceutical composition together with a solid or liquid pharmaceutical carrier suitable for oral administration, injection, etc. Such a pharmaceutical composition includes, for example, a solid preparation such as a tablet, granule, powder, capsule, etc., a liquid preparation such as a solution, suspension, emulsion, etc., and a lyophilizate preparation, and the like. These preparations can be prepared in a conventional manner. In addition, the preventive or therapeutic agent for diabetes or obesity of the present invention may optionally contain any pharmaceutically or pharmacologically acceptable solid or liquid carriers, additives and the like.

Examples of the carrier described above are glucose, lactose, sucrose, starch, mannitol, dextrin, glycerides of fatty acids, polyethylene glycols, hydroxyethyl starch, ethylene glycols, polyoxyethylene sorbitan fatty acid esters, gelatin, albumin, amino acids, water and a physiological saline solution. If necessary, conventional additives such as stabilizers, moisturizers, emulsifiers, binders, tonicity agents, etc. can be appropriately added to the preventive or therapeutic agent for diabetes or obesity of the present invention.

The above additives are not particularly limited as long as they are ordinarily used purposes depending upon purposes to meet the purposes. Examples of the additives include flavoring agents, sugars, sweetening agents, dietary fibers, vitamins, amino acids such as a monosodium glutamate (MSG), etc., nucleic acids such as an inosine monophosphate (IMP), etc., inorganic salts such as sodium chloride, water, and the like.

The preventive or therapeutic agent for diabetes or obesity of the present invention can be used in any form such as dry powder, paste, a solution, etc., irrespective of physical properties. The preventive or therapeutic agent for diabetes or obesity of the present invention can also be used in medical drugs, quasi drugs, food products, reagents, or the like.

The amount of the preventive or therapeutic agent for diabetes or obesity of the present invention can be appropriately adjusted depending upon each purpose. For example, in the case that they are orally administered to a target subject, a total amount of the glutamic acid derivative represented by formula (I) or pharmaceutically acceptable salts thereof is preferably 0.01 mg to 10 g in single administration, and more preferably 0.1 mg to 1 g, per kg of body weight.

The frequency of administration is not particularly limited, and the agent can be administered once or several times per day.

Where the preventive or therapeutic agent for diabetes or obesity of the present invention is used in food or reagent, the amount is preferably 0.000001 g to 10 g per one prescription, and more preferably 0.00001 g to 1 g per one prescription.

The amount of the glutamic acid derivative represented by formula (I) or its pharmaceutically acceptable salt in the preventive or therapeutic agent for diabetes or obesity of the present invention is not particularly limited so long as the amount meets the use range described above, and is preferably 0.000001% by weight to 99.9999% by weight, more preferably 0.00001% by weight to 99.999% by weight, and particularly preferably 0.0001% by weight to 99.99% by weight, based on the dry weight.

The preventive or therapeutic agent for diabetes or obesity of the present invention may further contain one or more known substances having the CaSR agonist activity.

Examples of the known substances having the CaSR agonist activity include cations such as calcium, gadolinium, etc.; basic peptides such as polyarginine, polylysine, etc.; polyamines such as putrescine, spermine, spermidine, etc.; proteins such as protamine, etc.; amino acids such as phenylalanine, etc.; peptides such as glutathione, etc.; and analogues of cinacalcet, but they are not limited thereto.

In addition to the known substances having the CaSR agonist activity, the preventive or therapeutic agent for diabetes or obesity of the present invention may also contain any known substance depending upon purposes.

The preventive or therapeutic agent for diabetes or obesity of the present invention may also be used as foods and beverages or supplements which are effective for the treatment or prevention of disorders, i.e., diabetes or obesity, associated with the secretion of GLP-1 or CCK. The agent can be prepared into foods and beverages indicating on the container or package thereof that there are the therapeutic or preventive effects on, e.g., diabetes or obesity. The form of the foods and beverages is not particularly limited, and the foods and beverages can be produced by the same manner as in conventional food products, using the same materials as used in producing conventional food products, except that the compound of the present invention is formulated. Examples of food products include seasonings; beverages such as juice and milk; confectionery; jellies; health foods; processed agricultural products; processed animal products such as milk and cheese; food supplements, and the like.

When the preventive or therapeutic agent for diabetes or obesity, which comprises the glutamic acid derivative of the present invention represented by formula (I) above or pharmaceutically acceptable salts thereof, is added to foods and beverages, the form is not limited in terms of physical properties such as dry powder, paste, a solution, etc.

(Representative Processes of Synthesizing the Glutamic Acid Derivative Represented by General Formula (I))

The representative methods of producing the compound of the present invention are illustrated below.

In the following production methods, it is sometimes effective in terms of processing technology to previously replace a functional group with an appropriate protective group, i.e. a group capable of easily converting into the functional group at the stage of the starting material or its intermediate, depending upon kind of the functional group. Then, the protective group is removed, if necessary, to obtain the intended compound. Such functional groups include, for example, an amino group, a hydroxyl group, a carboxyl group, etc. Examples of the protective groups for these functional groups include t-butoxycarbonyl (Boc), benzyloxycarbonyl (Z or Cbz), 9-fluorenylmethoxycarbonyl (Fmoc), etc. as a protective group for the amino group; t-butyl (tBu), benzyl (Bn or Bzl), etc. as protective groups for the carboxyl group; and protective groups described in Protective Groups in Organic Synthesis, third edition (T. W. Green and P. G. M. Wuts, JOHN WILLY & SONS, INC.). These protective groups may be appropriately used depending upon reaction conditions. The introduction and deprotection of these protective groups can be conducted at the right time in accordance with the procedures described in the reference book described above. For example, functional groups represented by Prot1 and Prot2 in the following methods 1 and 2 indicate that they are used as protective groups, but functional group is not limited thereto.

(Production Method 1)

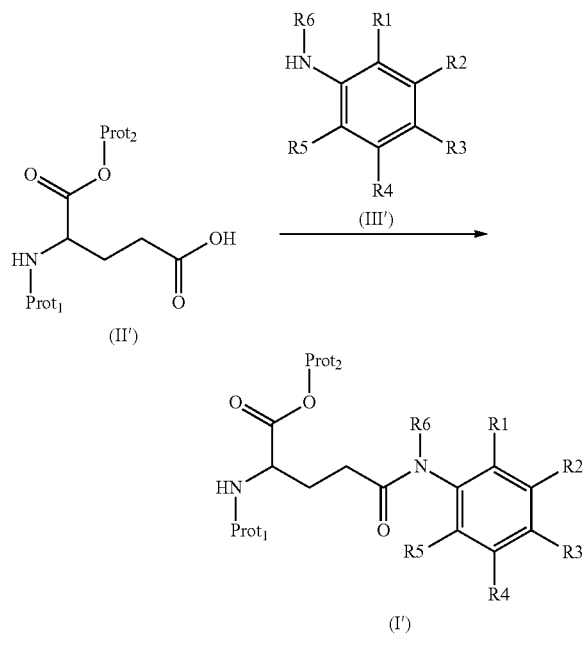

Production Method 1 is the reaction for producing the compound (I') by condensation between the carboxylic acid and the amine using the compound (II') and the compound (III').

The reaction can be carried out in a conventional manner using the equivalent of the compound (II') and the amine derivative (III') or an excess of either one in the presence of a condensing agent. Examples of the condensing agent which are advantageously used include N,N-dicyclohexylcarbodiimide (DCC), 1-ethyl-3-[3-(N,N-dimethylamino)propyl]carbodiimide (EDCI or WSC), O-benzotriazol-1-yl-N,N,N',N'-tetramethyluronium hexafluorophosphate (HBTU), carbonyldiimidazole (CDI), 4-(4,6-dimethoxy-1,3,5-triazin-2-yl)-4-methylmorpholinium chloride (DMTMM), 2-(7-azabenzotriazol-1-yl)-N,N,N',N'-tetramethyluronium hexafluorophosphate (HATU), etc. These condensing agents are used in an equivalent or excess amount based on the carboxylic acid. A solvent that is inert to the reaction, e.g., N,N-dimethylformamide (DMF), dioxane, water, methanol, ethanol, tetrahydrofuran (THF), dichloromethane, dichloroethane, diethyl ether, chloroform, dimethoxyethane (DME), ethyl acetate, toluene, acetonitrile, dimethylsulfoxide (DMSO), a solvent mixture thereof, etc., may be used as a solvent. Preferably, solvents are appropriately chosen depending on a starting material, kind of a condensing agent, and the like. The reaction can proceed smoothly in the presence of a base such as triethylamine, diisopropylethylamine, (DIEA) N-methylmorpholine, pyridine, 4-dimethylaminopyridine, etc.; or by reacting these bases as a solvent. Though the reaction is usually performed while cooling to at room temperature, it is sometimes preferred to conduct the reaction under heating depending on the conditions of the condensation reaction.

The compound (I') can also be produced by a process of introducing the carboxylic acid into its active derivative and then condensing the derivative with the amine. In this case, the compound (II') and the amine derivative (III') are used in an equivalent amount or in an excess amount of either one. Examples of the active derivative of the carboxylic acid include a phenol compound such as p-nitrophenol, etc.; an activated ester obtained by reacting a N-hydroxyamine compound such as 1-hydroxysuccinimide (HOSu), 1-hydroxybenzotriazole (HOBt) and 7-aza-1-hydroxybenzotriazole (HOAt); a mixed acid anhydride obtained by reacting a monoalkyl carbonate and an organic acid; a phosphoric mixed acid anhydride obtained by reacting diphenylphosphoryl chloride and N-methylmorpholine; an acid azide obtained by sequentially reacting an ester with a hydrazine and an alkyl nitrite; an acid halide such as an acid chloride, an acid fluoride, etc.; and a symmetrical acid anhydride, and the like.

Where the active derivative of the carboxylic acid is synthesized, an activating reagent is used in an equivalent or excess amount based on the compound (II'). Any reaction can be used even under reaction conditions other than those in the case above, so long as it is a reaction that forms an amide bond.

The glutamic acid derivative of the present invention represented by formula (I) wherein E represents groups other than hydroxyl group can also be produced by a reaction for selectively removing Prot1 from, e.g., the compound (I') protected. Alternatively, a process which comprises deprotecting Prot1 and Prot2 and then esterifying, e.g., in an alcohol solvent such as methanol in the presence of an acid catalyst such as hydrogen chloride, or a process which comprises selectively removing Prot2 alone, reacting with an alcohol in the presence of a condensing agent for esterification as in the process above and then removing Prot1, if necessary.

(Production Method 2)

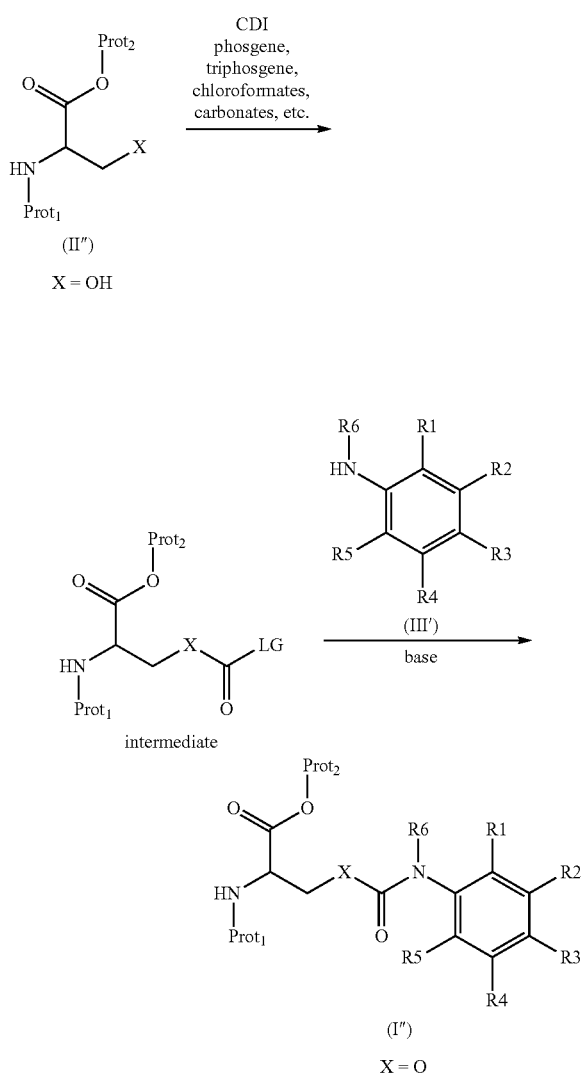

This method involves a reaction which comprises obtaining the intermediate from the compound (II″) and then reacting the resulting intermediate with the compound (III′) to produce the compound (I″).

According to the reaction, the intermediate can be obtained by reacting the compound (II″) with an equivalent or a little excess amount of a reagent such as N,N-carbonyldiimidazole, phosgene, triphosgene, benzyl chloroformate, methyl carbonate, etc. In this case, the reaction is carried out preferably in a solvent inert to the reaction, e.g., N,N-dimethylformamide (DMF), dioxane, tetrahydrofuran (THF), dichloromethane, dichloroethane, diethyl ether, chloroform, dimethoxyethane (DME), ethyl acetate, toluene, acetonitrile, dimethylsulfoxide (DMSO), or a solvent mixture thereof, or the like. Though the reaction is usually conducted while cooling to at room temperature, it is sometime preferred to perform the reaction with heating depending on the reagent and compound. The resulting intermediate is transferred to a preferable solvent, if necessary, and the reaction is carried out using the intermediate and the compound (III′) in an equivalent or a little excessive amount of either one. The reaction can also be performed in the presence of an organic base such as triethylamine or an inorganic base such as potassium carbonate, etc. Though the reaction is usually conducted with cooling to heating at about 100° C., it is sometimes necessary to conduct the reaction with further heating, depending on the compound. In addition to the method above, any reaction can be used so long as it is a reaction of forming the carbamate.

The glutamic acid derivative of the present invention represented by formula (I) wherein E represents groups other than hydroxyl group can be produced by a reaction of selectively removing $Prot_1$ from, e.g., the compound (I″) protected. Alternatively, a process which comprises deprotecting $Prot_1$ and $Prot_2$ and then esterifying, e.g., in an alcohol solvent such as methanol in the presence of an acid catalyst such as hydrogen chloride, or a process which comprises selectively removing $Prot_2$ alone, reacting with an alcohol in the presence of a condensing agent for esterification as in the method above and then removing $Prot_1$, if necessary.

(Production Method 3)

The compound of the present invention thus produced can be used as it is in a free form or its salt form, or can be isolated or purified by conventional chemical procedures in the art, e.g., extraction, precipitation, fractional chromatography, fractional crystallization, recrystallization, etc. The salts of the compound can be produced by applying a conventional salt-forming reaction to the free form of the compound of the present invention.

Where the compound of the present invention has asymmetric carbons, its optical isomers exist. The optical isomers can be produced by the procedures of converting the compound into a diastereomeric salt with an optically active acid or base followed by fractional crystallization, optical resolution in a conventional manner such as column chromatography, etc., synthesis using an optically active raw compound, or the like.

In formula (I), configuration of the carbon atom to which E-CO— and the amino group bind is preferably the S-configuration.

EXAMPLES

Hereinafter, the present invention will be described in more detail with reference to EXAMPLES, but is not deemed to be limited thereto.

As used herein, the conventional manner is intended to mean the procedures generally used as chemical operations represented by liquid separation, drying, filtration and concentration.

As used herein, the purification step A is intended to mean the procedures which comprises applying a crude product obtained in a conventional manner to a reversed phase high-performance liquid chromatography using octadecylsilyl silica gel (ODS) as a filler, followed by elution with a solution mixture of water and acetonitrile containing 0.1% (v/v) trifluoroacetic acid, concentrating and freeze-drying the fraction of interest.

Hereinafter, synthesis of the representative compounds of the present invention listed in TABLE 1 is described in more detail, by referring to EXAMPLES but the compound of the present invention is not deemed to be limited to these EXAMPLES.

TABLE 1

$$\text{(I)}$$

Structure: HOOC-CH(NH₂)-CH₂-X-C(=O)-N(R6)-Ar where Ar has R1, R2, R3, R4, R5 substituents.

| Comp. No. | R₁ | R₂ | R₃ | R₄ | R₅ | R₆ | X |
|---|---|---|---|---|---|---|---|
| 1 | H | SO₃H | H | H | H | H | CH₂ |
| 2 | H | SO₃H | OMe | H | H | H | CH₂ |
| 3 | H | SO₃H | H | H | OMe | H | CH₂ |
| 4 | H | SO₃H | Me | H | Me | H | CH₂ |
| 5 | H | SO₃H | Me | H | H | H | CH₂ |
| 6 | H | SO₃H | H | NO₂ | OH | H | CH₂ |
| 7 | OH | SO₃H | H | Cl | H | H | CH₂ |
| 8 | H | SO₃H | H | H | OH | H | CH₂ |
| 9 | H | SO₃H | Cl | H | H | H | CH₂ |
| 10 | OH | SO₃H | H | H | H | H | CH₂ |
| 11 | H | SO₃H | OH | H | H | H | CH₂ |
| 12 | H | SO₃H | H | H | H | CH₂ | CH₂ |
| 13 | H | SO₃H | H | H | H | H | O |
| 14 | H | CO₃H | H | H | H | H | CH₂ |
| 15 | OH | CO₃H | H | H | H | H | CH₂ |
| 16 | H | CO₃H | H | Br | H | H | CH₂ |
| 17 | H | PO(OMe)OH | H | H | H | H | CH₂ |
| 18 | H | PO(OH)₂ | H | H | H | H | CH₂ |
| 19 | H | NO₂ | H | H | H | H | CH₂ |
| 20 | H | H | H | H | H | H | CH₂ |

Example I

Synthesis Example 1

Synthesis of N⁵-(3-sulfophenyl)-L-glutamine (Compound No. 1)

Boc-Glu-OtBu (75 mg, 0.247 mmol), HATU (112 mg, 0.296 mmol) and HOAt (41 mg, 0.296 mmol) were dissolved in 1 ml of DMF, and triethylamine (52 μl) was added to the solution, followed by stirring at room temperature for 10 minutes. 3-Sulfoaniline (43 mg, 0.247 mmol) was added thereto and stirred at room temperature overnight. After the solvent was removed by distillation, the mixture was purified according to the purification step A. The resulting intermediate was dissolved in 2 ml of trifluoroacetic acid. After stirring for 3 hours at room temperature, the solvent was removed by distillation. The product was purified according to the purification step A to give the title compound.

Yield amount: 30.8 mg (0.10 mmol), yield: 41%
$^1$H-NMR (D$_2$O, 300 MHz): δ 7.89 (s, 1H), 7.67-7.62 (m, 2H), 7.58-7.53 (m, 1H), 3.99 (t, 1H, J=6.4 Hz), 2.73-2.66 (m, 2H), 2.33-2.25 (m, 2H)
ESI (m/z): 303 [M+H]$^+$, 301 [M−H]$^−$ Synthesis Example 2

Synthesis of N⁵-(4-methoxy-3-sulfophenyl)-L-glutamine (Compound No. 2)

The title compound was obtained in the same way except that p-anisidine-3-sulfonic acid was used in place of 3-sulfoaniline of SYNTHESIS EXAMPLE 1.
Yield amount: 24.7 mg, yield: 23%
1H-NMR (D$_2$O, 300 MHz): δ 7.96 (s, 1H), 7.53 (d, 1H), 7.04 (d, 1H), 3.98 (t, 1H), 3.78 (s, 3H), 2.63-2.52 (m, 2H), 2.30-2.05 (m, 2H)
ESI (m/z): 333 [M+H]$^+$ Synthesis Example 3

Synthesis of N⁵-(2-methoxy-5-sulfophenyl)-L-glutamine (Compound No. 3)

The title compound was obtained in the same way except that o-anisidine-5-sulfonic acid was used in place of 3-sulfoaniline of SYNTHESIS EXAMPLE 1.
Yield amount: 75.7 mg, yield: 69%
1H-NMR (D$_2$O, 300 MHz): δ 7.65 (s, 1H), 7.45 (d, 1H), 7.04 (d, 1H), 3.96 (t, 1H), 3.79 (s, 3H), 2.80-2.50 (m, 2H), 2.25-2.10 (m, 2H)
ESI (m/z): 333 [M+H]$^+$ Synthesis Example 4

Synthesis of N⁵-(2,4-dimethyl-5-sulfophenyl)-L-glutamine (Compound No. 4)

The title compound was obtained in the same way except that sodium 2,4-dimethylaniline-5-sulfonate was used in place of 3-sulfoaniline of SYNTHESIS EXAMPLE 1.
Yield amount: 70.3 mg, yield: 64%
1H-NMR (D$_2$O, 300 MHz): δ 7.55 (s, 1H), 7.17 (s, 1H), 3.97 (t, 1H), 2.67-2.55 (m, 2H), 2.43 (s, 3H), 2.30-2.15 (m, 2H), 2.08 (s, 3H)
ESI (m/z): 331 [M+H]$^+$ Synthesis Example 5

Synthesis of N⁵-(4-methyl-3-sulfophenyl)-L-glutamine (Compound No. 5)

The title compound was obtained in the same way except that 5-amino-2-methylbenzene-1-sulfonic acid was used in place of 3-sulfoaniline of SYNTHESIS EXAMPLE 1.
Yield amount: 79.3 mg, yield: 76%
1H-NMR (D$_2$O, 300 MHz): δ 7.76 (s, 1H), 7.34 (d, 1H), 7.24 (d, 1H), 3.93 (t, 1H), 2.60-2.45 (m, 2H), 2.44 (s, 3H), 2.30-2.00 (m, 2H)
ESI (m/z): 317 [M+H]$^+$ Synthesis Example 6

Synthesis of N⁵-(2-hydroxy-3-nitro-5-sulfophenyl)-L-glutamine (Compound No. 6)

The title compound was obtained in the same way except that 3-amino-4-hydroxy-5-nitrobenzenesulfonic acid was used in place of 3-sulfoaniline of SYNTHESIS EXAMPLE 1.
Yield amount: 73.8 mg, yield: 62%
1H-NMR (D$_2$O, 300 MHz): δ 8.37 (s, 1H), 8.24 (s, 1H), 3.94 (t, 1H), 2.64-2.70 (m, 2H), 2.09-2.23 (m, 2H)
ESI (m/z): 364 [M+H]$^+$ Synthesis Example 7

Synthesis of N⁵-(5-chloro-2-hydroxy-3-sulfophenyl)-L-glutamine (Compound No. 7)

Boc-Glu-OtBu (100 mg, 0.33 mmol) and HOBt monohydrate (65.6 mg, 0.43 mmol) were dissolved in 2 ml of DMF, and triethylamine (0.137 ml) was added to the solution. After cooling to 0° C., diisopropylcarbodiimide (66.4 μl, 0.43 mmol) and 2-amino-4-chlorophenol-6-sulfonic acid (73.7 mg, 0.33 mmol) were added, followed by stirring at room temperature overnight. After the solvent was removed by distillation, the mixture was purified according to the purification step A. The resulting intermediate was dissolved in 2 ml of TFA. The solution was stirred at room temperature for 2 hours, and 2 ml of methylene chloride was added thereto. The precipitate was taken out by filtration to give the title compound.

Yield amount: 16.8 mg, yield: 14.4%
$^1$H-NMR (DMSO-d6, 300 MHz): δ 11.07 (s, 1H), 9.39 (s, 1H), 8.20-8.40 (br, 2H), 8.02 (s, 1H), 7.14 (s, 1H), 3.95 (t, 1H, J=6.4 Hz), 2.64 (m, 2H), 2.07 (m, 2H)
ESI (m/z): 353 [M+H]$^+$ Synthesis Example 8

Synthesis of $N^5$-(2-hydroxy-5-sulfophenyl)-L-glutamine (Compound No. 8)

The title compound was obtained in the same way except that 2-aminophenol-4-sulfonic acid was used in place of 2-amino-4-chlorophenol-6-sulfonic acid of SYNTHESIS EXAMPLE 7.

Yield amount: 31.5 mg, yield: 30%
1H-NMR (D$_2$O, 300 MHz): δ 7.77 (s, 1H), 7.44 (d, 1H), 6.94 (d, 1H), 4.00-3.85 (m, 1H), 2.65-2.57 (m, 2H), 2.19-2.10 (m, 2H)
ESI (m/z): 319 [M+H]$^+$ Synthesis Example 9

Synthesis of $N^5$-(4-chloro-3-sulfophenyl)-L-glutamine (Compound No. 9)

The title compound was obtained in the same way except that 4-chloroaniline-3-sulfonic acid (68.4 mg) was used in place of 2-amino-4-chlorophenol-6-sulfonic acid of SYNTHESIS EXAMPLE 7.

Yield amount: 47.8 mg, yield: 43%
1H-NMR (D$_2$O, 300 MHz): δ 7.91 (s, 1H), 7.50-7.45 (m, 2H), 4.00-3.85 (m, 1H), 2.60-2.40 (m, 1H), 2.25-2.15 (m, 2H)
ESI (m/z): 337 [M+H]$^+$ Synthesis Example 10

Synthesis of $N^5$-(2-hydroxy-3-sulfophenyl)-L-glutamine (Compound No. 10)

Z-Glu-OBn (371 mg, 1 mmol) was dissolved in methylene chloride (1 ml), and CDI (180 mg, 1.1 mmol) was added to the solution. The mixture was stirred at room temperature for 30 minutes. 2-Amino-4-chlorophenol-6-sulfonic acid (223 mg, 1 mmol) and THF (1 ml) were added to the mixture. The mixture was then stirred overnight at room temperature. After the solvent was removed by distillation, the mixture was purified in accordance with the purification step A. The resulting intermediate was dissolved in a methanol-water solvent mixture. A catalytic amount of Pd/C was added to the solution. The mixture was stirred overnight at room temperature in a hydrogen atmosphere. After the catalyst was filtered off, the solvent was removed by distillation. The mixture was purified according to the purification step A to give the title compound.

Yield amount: 120 mg (0.40 mmol), yield: 40%
1H-NMR (D$_2$O, 300 MHz): δ 7.67 (d, 1H, J=7.9 Hz), 7.62 (d, 1H, J=8.2 Hz), 7.07 (dd, 1H, J=7.9 Hz, 8.2 Hz), 3.92-3.97 (m, 1H), 2.59-2.64 (m, 2H), 2.25-2.20 (m, 2H)
ESI (m/z): 303 [M+H]$^+$ Synthesis Example 11

Synthesis of $N^5$-(4-hydroxy-3-sulfophenyl)-L-glutamine (Compound No. 11)

Boc-Glu-OtBu (100 mg, 0.33 mmol) was dissolved in methylene chloride (1 ml) and THF (1 ml), and CDI (65 mg, 1.1 mmol) was added to the solution. The mixture was stirred for 30 minutes at room temperature. Sodium 5-amino-2-hydroxybenzenesulfonate (77 mg, 0.33 mmol) was added to the mixture and stirred overnight at room temperature. After the solvent was removed by distillation, the mixture was purified in accordance with the purification step A. The resulting intermediate was dissolved in 2 ml of TFA. After stirring for 3 hours at room temperature, the solvent was distilled off. The mixture was purified according to the purification step A to give the title compound.

Yield amount: 2 mg
ESI (m/z): 319 [M+H]$^+$

Synthesis Example 12

Synthesis of $N^5$-methyl-$N^5$-(3-sulfophenyl)-L-glutamine (Compound No. 12)

Step 1: Synthesis of 1 3-[(2-nitrophenyl)sulfonyl]aminobenzenesulfonic acid

3-Aminobenzenesulfonic acid (346.3 mg, 2 mmol) was dissolved in 2.5 ml of methylene chloride. After cooling to 0° C., 2-nitrophenylbenzenesulfonyl chloride (443.2 mg, 2 mmol) and N,N-diisopropylethylamine (697 µA 4 mmol) were added to the solution. After stirring at room temperature for an hour, the solvent was distilled off. The mixture was purified according to the purification step A to give the title compound.

Yield amount: 460 mg (1.29 mmol), yield: 64%
1H-NMR (DMSO-d6, 300 MHz): δ 7.02-7.83 (m, 8H)
ESI (m/z): 359 [M+H]$^+$ Step 2: Synthesis of $N^5$-methyl-$N^5$-(3-sulfophenyl)-L-glutamine Potassium carbonate (177 mg, 1.28 mmol), DMF (2 ml) and MeI (60 ml) were added to the compound (230 mg, 0.65 mmol) obtained in Step 1. The mixture was stirred at 40° C. for 6 hours. Potassium carbonate (44.3 mg) and MeI (40 µL) were supplemented and stirred overnight. After the solvent was removed by distillation, the purification step A was applied to give the crude product of 3-{methyl[(2-nitrophenyl)sulfonyl]amino}benzenesulfonic acid (160 mg). This crude product (144 mg, 0.39 m ml) was dissolved in DMF (3 ml), and cesium carbonate (126 mg, 0.39 mmol) and thiophenol (40 µl, 0.39 mmol) were added to the solution. The mixture was stirred at 50° C. overnight. After the solvent was removed by distillation, the purification step A was applied to give the crude product of 3-(methylamino)benzenesulfonic acid (84.1 mg).

The title compound was obtained in the same way except that the crude product of 3-(methylamino)benzenesulfonic acid was used in place of 3-sulfoaniline of SYNTHESIS EXAMPLE 1.

Yield amount: 5.14 mg
ESI (m/z): 317 [M+H]$^+$

Synthesis Example 13

Synthesis of O-{[(3-sulfophenyl)amino]carbonyl}-L-serine (Compound No. 13)

Boc-Ser-OtBu (200 mg, 0.77 mmol) was dissolved in 3 ml of methylene chloride and cooled to 0° C. N,N'-Carbonyldiimidazole (124 mg, 0.77 mmol) was added to the solution and stirred at room temperature for 2 hours. After the solvent was removed by distillation, 3-aminobenzenesulfonic acid (132.6 mg, 0.77 mmol), 2 ml of DMF and 0.4 ml of diisopropylethylamine were added and stirred at 70° C. overnight. The solvent was removed by distillation and the mixture was purified according to the purification step A to give the intermediate. The resulting intermediate was dissolved in 1 ml of TFA and stirred at room temperature for 2 hours. The solvent was removed by distillation, and the mixture was purified according to the purification step A to give the title compound.

Yield amount: 1.39 mg yield: 0.6%
ESI (m/z): 304 [M+H]$^+$

Synthesis Example 14

Synthesis of 3-(L-γ-glutamylamino)benzoic acid (Compound No. 14)

Boc-Glu-OtBu (100 mg, 0.33 mmol) and HATU (150.4 mg, 0.40 mmol) were dissolved in 2 ml of DMF, and triethylamine (68.5 μl) was added to the solution. The mixture was then stirred for 10 minutes. Ethyl 3-aminobenzoate (49.2 mg, 0.33 mmol) was added to the mixture and stirred overnight. After liquid separation was effected with ethyl acetate and 1M aqueous sodium hydroxide solution, the organic layer was washed sequentially with 1M aqueous sodium hydroxide solution, 1M hydrochloric acid and aqueous saturated sodium chloride solution (brine), followed by drying over sodium sulfate. After the solvent was distilled off, the resulting residue was dissolved in 2 ml of THF, 1 ml of ethanol and 1 ml of water. Lithium hydroxide monohydrate (13.5 mg, 0.32 mmol) was added to the solution. After stirring for 5 hours, 4.5 mg of lithium hydroxide was added to the mixture and stirred overnight. After it was confirmed that the reaction was completed, pH of the reaction solution was adjusted to 2 with 1M hydrochloric acid and the solvent was distilled off. After 3 ml of TFA was added to the resulting residue, the mixture was stirred at room temperature for 5 hours and the solvent was removed by distillation. The mixture was then purified according to the purification step A to give the title compound.

Yield amount: 54.17 mg, yield: 61%
1H-NMR (D$_2$O, 300 MHz): δ 7.92 (s, 1H), 7.72 (d, 1H, J=7.5 Hz), 7.55 (d, 1H, J=9 Hz), 7.42 (dd, 1H, J=7.5, 9.0 Hz), 4.00-3.80 (m, 1H), 2.58-2.54 (m, 2H), 2.20-2.15 (m, 2H)
ESI (m/z): 267 [M+H]$^+$

Synthesis Example 15

Synthesis of 3-(L-γ-glutamylamino)-2-hydroxybenzoid acid (Compound No. 15)

The title compound was obtained in the same way except that ethyl 3-amino-2-hydroxybenzoate was used in place of ethyl 3-aminobenzoate of SYNTHESIS EXAMPLE 14.

Yield amount: 34.1 mg yield: 37%
1H-NMR (D$_2$O, 300 MHz): δ 7.70-7.60 (m, 2H), 6.87 (t, 1H), 3.91 (t, 1H), 2.63-2.55 (m, 2H), 2.20-2.10 (m, 2H)
ESI (m/z): 283 [M+H]$^+$

Synthesis Example 16

Synthesis of 3-bromo-5-(L-γ-glutamylamino)benzoic acid (Compound No. 16)

The title compound was obtained in the same way except that methyl 3-amino-5-bromobenzoate was used in place of ethyl 3-aminobenzoate of SYNTHESIS EXAMPLE 14.

Yield amount: 16.8 mg
1H-NMR (D$_2$O, 300 MHz): δ 7.80-7.85 (s*2, 2H), 3.75-3.90 (m, 1H), 2.45-2.55 (m, 2H), 2.10-2.20 (m, 2H)
ESI (m/z): 345, 347 [M+H]$^+$

Synthesis Example 17

Synthesis of N$^5$-{3-[hydroxy(methoxy)phosphoryl]phenyl}-L-glutamine (Compound No. 17)

1-Iodo-3-nitrobenzene (249 mg, 1 mmol) was dissolved in 10 ml of acetonitrile, and tetrakistriphenylphosphine palladium (58 mg, 3 mol %), dimethyl phosphite (0.138 ml, 1.5 mmol) and triethylamine (0.28 ml, 2 mmol) were added to the solution. The mixture was stirred at 70° C. overnight. After the solvent was removed by distillation, the mixture was purified according to the purification step A to give the mixture of monomethyl and dimethyl (3-nitrophenyl)phosphonate (0.222 g). The resulting monomethyl phosphonate was dissolved in 10 ml of methanol and a catalytic amount of Pd/C was added thereto. The mixture was stirred in a hydrogen atmosphere overnight. The catalyst was filtered off and the solvent was removed by distillation to give the mixture of monomethyl and dimethyl (3-aminophenyl)phosphonate.

Boc-Glu-OtBu (303 mg, 1 mmol), HOAt (136 mg, 1 mmol) and HATU (380 mg, 1 mmol) were dissolved in 1 ml of DMF, and triethylamine (0.278 ml) was added to the solution. Ten minutes after, the mixture of monomethyl and dimethyl (3-aminophenyl)phosphonate was added to the mixture. The mixture was stirred at room temperature overnight.

After the solvent was distilled off, the mixture was purified according to the purification step A to give the title compound.

Yield amount: 11.5 mg
1H-NMR (D$_2$O, 300 MHz): δ 7.50-7.90 (m, 4H), 4.14-4.18 (m, 1H), 3.56 (s, 1.5H), 3.52 (s, 1.5H), 2.68-2.74 (m, 2H), 2.280-2.37 (m, 2H)
ESI (m/z): 317 [M+H]$^+$

Synthesis Example 18

Synthesis of N$^5$-(3-phosphonophenyl)-L-glutamine (Compound No. 18)

To a mixture (170 mg) of monomethyl and dimethyl (3-nitrophenyl)phosphonate obtained as the intermediate in SYNTHESIS EXAMPLE 17 were added 4 ml of DMF and trimethylsilyl bromide (1 ml). The mixture was stirred at 60° C. for 2 hours. After the solvent was removed by distillation, the residue was dissolved in a solvent mixture of water and methanol. A catalytic amount of Pd/C was added to the solution and stirred overnight in a hydrogen atmosphere. The catalyst was filtered off and the solvent was removed by distillation to give the crude product of (3-aminophenyl)phosphonic acid.

Boc-Glu-OtBu (236 mg, 0.78 mmol), HOAt (127 mg, 0.936 mmol) and HATU (356 mg, 0.936 mmol) were dissolved in 1 ml of DMF, and triethylamine (0.21 ml) was added to the solution. Ten minutes after, the crude product of (3-aminophenyl)phosphonic acid was added and stirred at room temperature overnight. The solvent was distilled off and the mixture was purified in accordance with the purification step A to give the title compound.

Yield amount: 2.5 mg
ESI (m/z): 303 [M+H]$^+$

Synthesis Example 19

Synthesis of $N^5$-(3-nitrophenyl)-L-glutamine (Compound No. 19)

The title compound was obtained in the same way except that 3-nitroaniline was used in place of 3-sulfoaniline of SYNTHESIS EXAMPLE 1.

Yield amount: 61.6 mg, yield: 93%
1H-NMR (DMSO-d6, 300 MHz): δ 10.5 (s, 1H), 8.66 (s, 1H), 7.86-7.93 (m, 2H), 7.61 (t, 1H, J=8.2 Hz), 3.99 (t, 1H, J=6.2 Hz), 2.50-2.70 (m, 2H), 2.06-2.16 (m, 2H)
ESI (m/z): 268 [M+H]$^+$ Synthesis Example 20

N-γ-glutamyl-aniline (Compound No. 20)

Compound No. 20 used was purchased from Bachem Corp.

Hereinafter, the synthesis of other representative compounds shown in TABLE 2 is described in more detail by referring to EXAMPLES. However, the compound of the present invention is not deemed to be limited by these EXAMPLES.

TABLE 2

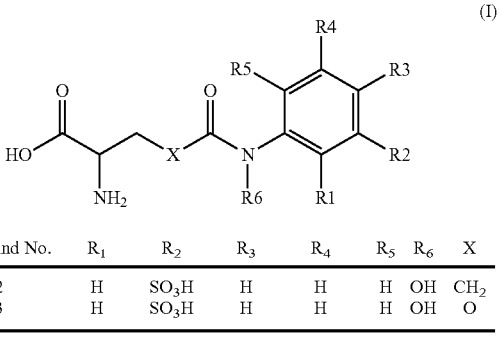

(I)

| Compound No. | R$_1$ | R$_2$ | R$_3$ | R$_4$ | R$_5$ | R$_6$ | X |
|---|---|---|---|---|---|---|---|
| 21 | H | SO$_3$H | Me | Cl | H | H | CH$_2$ |
| 22 | H | SO$_3$H | H | Cl | Me | H | CH$_2$ |
| 23 | OH | SO$_3$H | H | NO$_2$ | H | H | CH$_2$ |
| 24 | Cl | CO$_2$H | H | Cl | H | H | CH$_2$ |
| 25 | Cl | CO$_2$H | H | H | H | H | CH$_2$ |
| 26 | H | CO$_2$H | H | H | Cl | H | CH$_2$ |
| 27 | OMe | CO$_2$H | H | H | H | H | CH$_2$ |
| 28 | H | CO$_2$H | OH | H | H | H | CH$_2$ |
| 29 | H | CO$_2$H | H | H | Me | H | CH$_2$ |
| 30 | H | CO$_2$H | H | OH | H | H | CH$_2$ |
| 31 | Me | CO$_2$H | H | H | H | H | CH$_2$ |
| 32 | H | CO$_2$H | H | Cl | H | H | CH$_2$ |
| 33 | H | SO$_3$H | Me | Cl | H | H | O |
| 34 | OH | SO$_3$H | H | Cl | H | H | O |
| 35 | H | SO$_3$H | H | Cl | Me | H | O |
| 36 | OMe | SO$_3$H | H | Cl | H | H | O |
| 37 | H | SO$_3$H | H | H | Cl | H | CH$_2$ |
| 38 | H | H | SO$_3$H | Cl | H | H | CH$_2$ |
| 39 | SO$_3$H | H | H | Br | H | H | CH$_2$ |
| 40 | H | H | SO$_3$H | I | H | H | CH$_2$ |
| 41 | SO$_3$H | H | H | I | H | H | CH$_2$ |

TABLE 2-continued

| Compound No. | R$_1$ | R$_2$ | R$_3$ | R$_4$ | R$_5$ | R$_6$ | X |
|---|---|---|---|---|---|---|---|
| 42 | H | SO$_3$H | H | H | H | OH | CH$_2$ |
| 43 | H | SO$_3$H | H | H | H | OH | O |

Synthesis Example 21

Synthesis of $N^5$-(3-chloro-4-methyl-5-sulfophenyl)-L-glutamine (Compound No. 21)

After 1 ml of methylene chloride and 1 ml of THF were added to 303 mg (1 mmol) of Boc-Glu-OtBu hydrochloride and 180 mg (1.1 mmol) of CDI, 221 mg of 5-amino-3-chloro-2-methylbenzenesulfonic acid was further added to mixture. The mixture was stirred at room temperature overnight and then purified in accordance with the purification step A to give the protected form of the intended product. The obtained protected product was dissolved in 5 ml of trifluoroacetic acid. The solution was stirred for 2 hours. The solvent was distilled off and the mixture was purified in accordance with the purification step A to give the title compound.

1H-NMR (D$_2$O) δ: 7.71 (d, 1H), 7.60 (d, 1H), 3.93 (t, 1H), 2.50-2.57 (m, 2H), 2.47 (s, 3H), 2.10-2.20 (m, 2H)
ESI-MS: 349 [M−H]$^-$, 351 [M+H]$^+$

Synthesis Example 22

Synthesis of $N^5$-(3-chloro-2-methyl-5-sulfophenyl)-L-glutamine (Compound No. 22)

After 2 ml of DMF and 0.52 ml (3 mmol) of DIEA were added to 303 mg (1 mmol) of Boc-Glu-OtBu hydrochloride, 221 mg (1 mmol) of 3-amino-5-chloro-4-methylbenzenesulfonic acid, 160 mg (1.3 mmol) of HOAt and 410 mg (1.3 mmol) of HATU, the mixture was stirred at room temperature overnight. The reaction solution was diluted in water-acetonitrile and purified in accordance with the purification step A to give the protected form of the product. The protected product obtained was dissolved in 5 ml of trifluoroacetic acid and stirred for 2 hours. After the solvent was removed by distillation, the mixture was purified in accordance with the purification step A to give the title compound.

Yield amount: 150 mg
1H-NMR (D$_2$O) δ: 7.81 (d, 1H), 7.61 (d, 1H), 4.10 (t, 1H), 2.74-2.81 (m, 2H), 2.24-2.37 (m, 5H)
ESI-MS: 349 [M−H]$^-$, 351 [M+H]$^+$ Synthesis Example 23

Synthesis of $N^5$-(2-hydroxy-5-nitro-3-sulfophenyl)-L-glutamine (Compound No. 23)

The title compound was obtained in the same way except that 3-amino-2-hydroxy-5-nitrobenzenesulfonic acid was used in place of 3-amino-5-chloro-4-methylbenzenesulfonic acid of SYNTHESIS EXAMPLE 22.

Yield amount: 185 mg

1H-NMR (D$_2$O) δ: 8.55 (d, 1H, J=2.4 Hz), 8.29 (d, 1H, J=2.7 Hz), 3.95 (t, 1H, J=6.3 Hz), 2.66 (t, 2H, J=7.2 Hz), 2.10-2.30 (m, 2H)

ESI-MS: 362 [M–H]$^-$, 364 [M+H]$^+$

Synthesis Example 24

Synthesis of 2,5-dichloro-3-(L-γ-glutamylamino)benzoic acid (Compound No. 24)

Step 1

2,5-Dichloro-3-aminobenzoic acid, 206 mg (1.0 mmol), was dissolved in 4 ml of acetone, and 0.7 ml (1.4 mmol) of 2.0 M trimethylsilyl diazomethane solution in hexane was added to the solution. The mixture was stirred at room temperature for 1.5 hours. The solvent was removed by distillation to give methyl 2,5-dichloro-3-aminobenzoate.

Yield amount: 220 mg

Step 2

To 110 mg (0.5 mmol) of methyl 2,5-dichloro-3-aminobenzoate were added 190 mg (0.5 mmol) of HATU, 70 mg (0.5 mmol) of HOAt, 152 mg (0.5 mmol) of Boc-Glu-OtBu hydrochloride, 0.21 ml (1.5 mmol) of triethylamine and 2 ml of dichloromethane. The mixture was stirred at room temperature overnight.

The solvent was distilled off, and extraction was performed with ethyl acetate-water. The organic layer was treated with aqueous saturated sodium chloride solution (brine) and dried over sodium sulfate. Sodium sulfate was removed by filtration. After the solvent was removed by distillation, 5 ml of 1N sodium hydroxide solution was added and stirred at room temperature for 2 hours. Subsequently, 5 ml of trifluoroacetic acid was added and stirred at room temperature for 2 hours. The solvent was distilled off, and the mixture was purified in accordance with the purification step A to give the title compound.

Yield amount: 6.6 mg

1H-NMR (CD$_3$OD) δ: 8.08 (s, 1H), 7.56 (s, 1H), 3.95-4.01 (m, 1H), 2.76-2.82 (m, 2H), 2.20-2.30 (m, 2H)

ESI-MS: 333 [M–H]$^-$, 335 [M+H]$^+$

Synthesis Example 25

Synthesis of 2-chloro-3-(L-γ-glutamylamino)benzoic acid (Compound No. 25)

The title compound was obtained in the same way except that 2-chloro-3-aminobenzoic acid was replaced for the benzoic acid derivative used in SYNTHESIS EXAMPLE 24 (Synthesis of Compound No. 24).

Yield amount: 4.0 mg

1H-NMR (D$_2$O) δ: 7.47-7.56 (m, 1H), 7.39-7.46 (m, 1H), 7.27-7.32 (s, 1H), 3.81-387 (m, 1H), 2.59-2.65 (m, 2H), 2.12-2.21 (m, 2H)

ESI-MS: 299 [M–H]$^-$, 301 [M+H]$^+$

Synthesis Example 26

Synthesis of 4-chloro-3-(L-γ-glutamylamino)benzoic acid (Compound No. 26)

The title compound was obtained in the same way except that 4-chloro-3-aminobenzoic acid was replaced for the benzoic acid derivative used in SYNTHESIS EXAMPLE 24 (Synthesis of Compound No. 24).

Yield amount: 5.3 mg

1H-NMR (D$_2$O) δ: 8.03 (s, 1H), 7.76-7.79 (m, 1H), 7.52-7.55 (m, 1H), 3.78-3.84 (m, 1H), 2.59-2.65 (m, 2H), 2.12-2.22 (m, 2H)

ESI-MS: 299 [M–H]$^-$, 301 [M+H]$^+$

Synthesis Example 27

Synthesis of 2-methoxy-3-(L-γ-glutamylamino)benzoic acid (Compound No. 27)

HATU, 84 mg (0.2 mmol), 30 mg (0.2 mmol) of HOAt, 61 mg (0.2 mmol) of Boc-Glu-OtBu hydrochloride, 0.084 ml (0.6 mmol) of triethylamine and 1 ml of dichloromethane were added to 36 mg (0.2 mmol) of methyl 2-methoxy-3-aminobenzoate. The mixture was stirred at room temperature overnight.

The solvent was distilled off, and extraction was performed with ethyl acetate-water. The organic layer was treated with aqueous saturated sodium chloride solution (brine) and dried over sodium sulfate. Sodium sulfate was removed by filtration. After the solvent was removed by distillation, 5 ml of 1N aqueous sodium hydroxide solution was added and stirred at room temperature for 2 hours. Then, 5 ml of trifluoroacetic acid was added to the mixture. The mixture was stirred at room temperature for 2 hours. The solvent was distilled off, and the mixture was purified according to the purification step A to give the title compound.

Yield amount: 6.5 mg

1H-NMR (D$_2$O) δ: 7.69-7.71 (m, 1H), 7.56-7.59 (m, 1H), 7.13-7.18 (m, 1H), 3.87-3.93 (m, 1H), 3.68 (s, 3H), 2.60-2.66 (m, 2H), 2.12-2.22 (m, 2H)

ESI-MS: 295 [M–H]$^-$, 297 [M+H]$^+$

Synthesis Example 28

Synthesis of 6-hydroxy-3-(L-γ-glutamylamino)benzoic acid (Compound No. 28)

6-Methoxy-3-(L-γ-glutamylamino)benzoic acid was synthesized in the same way except that 6-methoxy-3-aminobenzoic acid was replaced for the benzoic acid derivative used in SYNTHESIS EXAMPLE 27 (Synthesis of Compound No. 27). The product was purified according to the purification step A to give the title compound as a by-product obtained in the course of synthesis.

Yield amount: 2.1 mg

ESI-MS: 280 [M–H]$^-$, 282 [M+H]$^+$

Synthesis Example 29

Synthesis of 4-methyl-3-(L-γ-glutamylamino)benzoic acid (Compound No. 29)

4-Methyl-3-nitrobenzoic acid, 500 mg, was dissolved in 5 ml of methanol and 10 ml of 4N hydrogen chloride-containing dioxane solution. After stirring for 2 days at room temperature, the solvent was distilled off to give the crude product. The crude product obtained was dissolved in 10 ml of methanol, and a catalytic amount of Pd/C was reacted there-with at room temperature overnight in a hydrogen atmosphere. The catalyst was separated by filtration and the solvent was removed by distillation to give the crude product. After 165 mg of the crude product, 303 mg (1 mmol) of Boc-Glu-OtBu hydrochloride and 400 mg (ca. 1.3 mmol) of HATU were dissolved in 1 ml of DMF, 0.26 ml of DIEA was added to the solution and stirred overnight. The reaction solution was diluted in water-acetonitrile and the mixture was purified in accordance with the purification step A to give 0.31 g of the protected product. To the protected product obtained were added 3 ml of THF, 1.5 ml of methanol and 1.5 ml of water. Then, 26 mg (0.82 mmol) of lithium hydroxide monohydrate was added to the mixture. After stirring for 2 hours, the solvent was distilled off. Again, 3 ml of THF, 1.5 ml of methanol and 1.5 ml of water were added and, 26 mg (0.82 mmol) of lithium hydroxide monohydrate was further added to the mixture. The mixture was stirred for 2 hours. After 2 ml of ethyl acetate was added, the solvent was distilled off. Next, 3 ml of trifluoroacetic acid was added and stirred at room temperature for 2 hours. The solvent was removed by distillation, and the mixture was purified according to the purification step A to give the title compound.

1H-NMR (D$_2$O) δ: 7.74-7.77 (m, 1H), 7.30-7.36 (m, 1H), 3.75-3.81 (m, 1H), 2.55-2.62 (m, 2H), 2.10-2.20 (m, 5H)

ESI-MS: 279 [M−H]$^-$, 281 [M+H]$^+$

Synthesis Example 30

Synthesis of
5-hydroxy-3-(L-γ-glutamylamino)benzoic acid
(Compound No. 30)

5-Methoxy-3-(L-γ-glutamylamino)benzoic acid was synthesized in the same way except that 5-methoxy-3-aminobenzoic acid was replaced for the benzoic acid derivative used in SYNTHESIS EXAMPLE 27 (Synthesis of Compound No. 27). The product was purified according to the purification step A to give the title compound as a by-product obtained in the course of synthesis.

Yield amount: 7.5 mg
ESI-MS: 280 [M−H]$^-$, 282 [M+H]$^+$

Synthesis Example 31

Synthesis of
3-(L-γ-glutamylamino)-2-methylbenzoid acid
(Compound No. 31)

The title compound was obtained in the same way except that 2-methyl-3-nitrobenzoic acid was replaced for the benzoic acid derivative used in SYNTHESIS EXAMPLE 29 (Synthesis of Compound No. 29).

Yield amount: 37 mg
1H-NMR (D$_2$O) δ: 7.56 (dd, 1H), 7.30 (dd, 1H), 7.23 (t, 1H), 3.82 (t, 1H), 2.5-2.62 (m, 2H), 2.21 (s, 3H), 2.10-2.29 (m, 2H)

ESI-MS: 279 [M−H]$^-$, 281 [M+H]$^+$

Synthesis Example 32

Synthesis of 5-chloro-3-(L-γ-glutamylamino)benzoic acid (Compound No. 32)

Step 1

After 8 ml of methanol and 2 ml of THF were added to 228 mg (1 mmol) of methyl 5-chloro-1,3-dibenzoate and 56 mg (1 mmol) of potassium hydroxide, the mixture was stirred at room temperature overnight. The reaction solution was concentrated under reduced pressure. Then, 4 ml of toluene, 0.12 ml (0.85 mmol) of triethylamine and 0.19 ml (0.88 mmol) of diphenylphosphorylazide were added and stirred at 50° C. for an hour. Subsequently, 0.19 ml (2 mmol) of t-butyl alcohol and 2 ml of toluene were added and stirred at 80° C. overnight. After cooling to room temperature, the mixture was extracted with ethyl acetate-water. The organic layer was treated with aqueous saturated sodium chloride solution (brine) and then dried over sodium sulfate. Sodium sulfate was removed by filtration. The solvent was distilled off and the mixture was purified in accordance with the purification step A to give methyl 5-chloro-3-aminobenzoate trifluoroacetate.

Yield amount: 30 mg

Step 2

HATU, 38 mg (0.1 mmol), 14 mg (0.1 mmol) of HOAt, 30 mg (0.1 mmol) of Boc-Glu-OtBu hydrochloride, 0.014 ml (0.1 mmol) of triethylamine and 1 ml of dichloromethane were added to 30 mg (0.1 mmol) of methyl 5-chloro-3-aminobenzoate. The mixture was stirred at room temperature overnight.

The solvent was removed by distillation, followed by extraction with ethyl acetate-water. The organic layer was treated with aqueous saturated sodium chloride solution (brine) and then dried over sodium sulfate. Sodium sulfate was removed by filtration. After the solvent was distilled off, 5 ml of 1N sodium hydroxide solution was added and stirred at room temperature for 2 hours. Subsequently, 5 ml of trifluoroacetic acid was added and stirred at room temperature for 2 hours. After the solvent was removed by distillation, the mixture was purified according to the purification step A to give the title compound.

Yield amount: 1.0 mg
1H-NMR (D$_2$O) δ: 7.54 (s, 1H), 7.48 (s, 1H), 7.45 (s, 1H), 3.96-4.00 (m, 1H), 2.50-2.56 (m, 2H), 2.12-2.20 (m, 2H)

ESI-MS: 299 [M−H]$^-$, 301 [M+H]$^+$

Synthesis Example 33

Synthesis of O-{[(3-chloro-4-methyl-5-sulfophenyl)amino]carbonyl}-L-serine (Compound No. 33)

Boc-Ser-OtBu, 100 mg (0.38 mmol), 86 mg (0.38 mmol) of 5-amino-3-chloro-2-methylbenzenesulfonic acid and 37 mg (0.0127 mmol) of triphosgene were suspended in 1 ml of methylene chloride, and 66 μl (0.76 mmol) of DIEA was added to the suspension. After stirring at room temperature overnight, the solvent was removed by distillation. The mixture was purified according to the purification step A to give the protected title compound. The protected product obtained was dissolved in 2 ml of trifluoroacetic acid and stirred for 2 hours. The solvent was then removed by distillation and the mixture was purified according to the purification step A to give the title compound.

Yield amount: 15.5 mg
1H-NMR (D$_2$O) δ: 7.67 (d, 1H), 7.57. (d, 1H), 4.51 (t, 2H), 4.15 (dd, 1H) 2.47 (s, 3H)

ESI-MS: 351 [M−H]$^-$, 353 [M+H]$^+$

Synthesis Example 34

Synthesis of Sodium 3-({R2S)-2-amino-2-carboxyethoxycarbonyl}amino)-5-chloro-2-hydroxy-benzenesulfonate (Compound No. 34)

The title compound was obtained in the same way except that 3-amino-5-chloro-2-hydroxybenzenesulfonic acid was replaced for the benzenesulfonic acid derivative used in SYNTHESIS EXAMPLE 33 (Synthesis of Compound No. 33), then 1 equivalent of 0.1N sodium hydroxide aqueous solution was added and freeze dried.
Yield amount: 15.1 mg
1H-NMR (D$_2$O) δ: 7.70 (s, 1H), 7.37 (d, 1H, J=2.6 Hz), 4.37-4.55 (m, 2H), 3.98 (dd, 1H, J=3.0, 5.3 Hz),
ESI-MS: 353 [M–H]$^-$, 355 [M+H]$^+$

Synthesis Example 35

Synthesis of O-{[(3-chloro-2-methyl-5-sulfophenyl)amino]carbonyl}-L-serine (Compound No. 35)

The title compound was obtained in the same way except that 3-amino-5-chloro-4-methylbenzenesulfonic acid was replaced for the benzenesulfonic acid derivative used in SYNTHESIS EXAMPLE 33 (Synthesis of Compound No. 33).
Yield amount: 3.9 mg
1H-NMR (D$_2$O) δ: 7.60-7.64 (m, 2H), 4.42-4.54 (m, 2H), 4.03 (dd, 1H, J=3.2, 4.8 Hz)
ESI-MS: 351 [M–H]$^-$, 353 [M+H]$^+$

Synthesis Example 36

Synthesis of O-{[(5-chloro-2-methoxy-3-sulfophenyl)amino]carbonyl}-L-serine (Compound No. 36)

Acetone (2 ml) was added to 30 mg of the protected product obtained in SYNTHESIS EXAMPLE 14 (Synthesis of Compound No. 14), and 1 ml of 2M trimethylsilyldiazomethane-containing hexane solution and 100 μl of triethylamine were further added to the mixture. After stirring for 20 minutes, the solvent was removed by distillation. The mixture was purified according to the purification step A to give the methylated product. The methylated product obtained was dissolved in 2 ml of trifluoroacetic acid and stirred at room temperature for 3 hours. After the solvent was removed by distillation, water was added and then freeze dried to give the title compound.
Yield amount: 1.48 mg
1H-NMR (D$_2$O) δ: 7.64 (brs, 1H), 7.27 (d, 1H, J=2.6 Hz), 4.25-4.22 (m, 2H), 3.80 (dd, 1H, J=3.1, 5.0 Hz), 3.52 (s, 3H)

Synthesis Example 37

Synthesis of N$^5$-(2-chloro-5-sulfophenyl)-L-glutamine (Compound No. 37)

To sodium 4-chloro-3-nitrobenzenesulfonate (1 mmol) were added 2 ml of methanol and 3 ml of water. A catalytic amount of 2% Pt-S/C was added to the mixture, followed by stirring at room temperature overnight in a hydrogen atmosphere. The catalyst was removed by filtration. After thoroughly drying, 303 mg (1 mmol) of Boc-Glu-OtBu hydrochloride, 163 mg (1.2 mmol) of HOAt, 456 mg (1.2 mmol) of HATU, 2 ml of DMF and 0.35 ml of DIEA were added and stirred at room temperature overnight. The reaction solution was diluted in water-acetonitrile and purified according to the purification step A to give the protected form of the title compound. The resulting protected product was dissolved in 3 ml of trifluoroacetic acid and stirred at room temperature for 2 hours. The solvent was then removed by distillation. The mixture was purified according to the purification step A to give the title compound.
Yield amount: 69.9 mg
1H-NMR (D$_2$O) δ: 7.85 (brs, 1H), 7.50-7.55 (m, 2H), 4.03 (t, 1H), 2.66 (t, 2H, J=7.1 Hz), 2.10-2.30 (m, 2H)
ESI-MS: 335 [M–H]$^-$, 337 [M+H]$^+$

Synthesis Example 38

Synthesis of N$^5$-(3-chloro-4-sulfophenyl)-L-glutamine (Compound No. 38)

Step 1

3-Chloroaniline, 0.4 ml, was slowly added to 4 ml of fuming sulfuric acid and stirred at room temperature overnight. While cooling to 0°, the reaction solution was poured onto water and the solid precipitated was separated by filtration. The solid filtered off was dissolved in 2N sodium hydroxide aqueous solution and conc. hydrochloric acid was then added to the solution to make the liquid acidic. The solid precipitated was taken by filtration to give the crude product of 4-amino-2-chlorobenzenesulfonic acid.
Yield amount: 80 mg

Step 2

The title compound was obtained in the same way except that the crude product of 4-amino-2-chlorobenzenesulfonic acid obtained in Step 1 was replaced for the benzenesulfonic acid derivative used in SYNTHESIS EXAMPLE 21 (Synthesis of Compound No. 21).
Yield amount: 40 mg
1H-NMR (D$_2$O) δ: 7.80 (d, 1H), 7.63 (d, 1H), 7.33 (dd, 1H), 3.94 (t, 1H), 2.50-2.60 (m, 2H), 2.10-2.22 (m, 2H)
ESI-MS: 337 [M+H]$^+$, 335 [M–H]$^-$

Synthesis Example 39

Synthesis of N$^5$-(5-bromo3-sulfophenyl)-L-glutamine (Compound No. 39)

The title compound was obtained in the same way as in Steps 1 and 2 except that 3-bromoaniline was replaced for the aniline derivative used in Step 1 of SYNTHESIS EXAMPLE 38 (Synthesis of Compound No. 38).
Yield amount: 9.9 mg
ESI-MS: 429 [M+H]$^+$, 427 [M–H]$^-$

Synthesis Example 40

Synthesis of N$^5$-(3-iodo-4-sulfophenyl)-L-glutamine (Compound No. 40)

The title compound was obtained in the same way as in Steps 1 and 2 except that 3-iodoaniline was replaced for the aniline derivative used in Step 1 of SYNTHESIS EXAMPLE 38 (Synthesis of Compound No. 38).

Yield amount:
1H-NMR (D$_2$O) δ: 8.12 (s, 1H), 7.84 (d, 1H), 7.44 (dd, 1H), 3.75-3.90 (m, 1H), 2.50-2.60 (m, 2H), 2.00-2.20 (m, 2H)
ESI-MS: 429 [M+H]$^+$, 427 [M–H]$^-$ Synthesis Example 41

Synthesis of N$^5$-(5-iodo-2-sulfophenyl)-L-glutamine (Compound No. 41)

The product was obtained as a stereoisomer in the synthesis of SYNTHESIS EXAMPLE 40.
1H-NMR (D$_2$O) δ: 8.11 (d, 1H), 7.63-7.66 (m, 1H), 7.48 (d, 1H), 3.80-3.90 (m, 1H), 2.58-2.66 (m, 2H), 2.10-2.24 (m, 2H)
ESI-MS: 429 [M+H]$^+$, 427 [M–H]$^-$ Synthesis Example 42

Synthesis of N$^5$-hydroxy-N$^5$-(3-sulfophenyl)-L-glutamine (Compound No. 42)

Zinc powders, 270 mg (4.3 mmol), and 106 mg (2 mmol) of ammonium chloride were suspended in 2 ml of a solvent mixture of methanol:water (1:1), and 450 mg (2 mmol) of sodium 2-nitrobenzenesulfonate was slowly added to the suspension. After heating to 65° C. and stirring for an hour, the impurities were removed by filtration. The resulting filtrate was removed by distillation to give the crude product of the hydroxylamine derivative. After 5 ml of DMF and 0.35 ml of DIEA were added to 450 mg (1.5 mmol) of Boc-Glu-OtBu hydrochloride, 230 mg (1.7 mmol) of HOAt and 646 mg (1.7 mmol) of HATU, the mixture was stirred for 10 minutes. The solution was added to the crude product previously obtained, followed by stirring overnight. The mixture was purified according to the purification step A to give the protected form of title compound. After 4 ml of TFA was added to the resulting protected product, the mixture was stirred for 2 hours. TFA was removed and the mixture was purified according to the purification step A to give the title compound.
Yield amount: 135 mg
1H-NMR (DMSO) δ: 10.65 (s, 1H), 10.04 (s, 1H), 7.20-8.40 (m, 7H), 3.90-4.10 (m, 1H), 2.60-3.00 (m, 2H), 1.90-2.20 (m, 2H)
ESI-MS: 317 [M–H]$^-$, 319 [M+H]$^+$ Synthesis Example 43

Synthesis of 0-{[hydroxy(3-sulfophenyl)amino]carbonyl}-L-serine (Compound No. 43)

Methylene chloride, 2 ml, and 0.35 ml of DIEA were added to 1 mmol of Boc-Ser-OtBu, the crude product of hydroxylamine obtained in SYNTHESIS EXAMPLE 42 and 100 mg (0.33 mmol) of triphosgene. The mixture was stirred at room temperature overnight. After the solvent was removed by distillation, the resulting residue was purified according to the purification step A to give the protected title compound. The protected product obtained was dissolved in 4 ml of TFA and stirred at room temperature for 3 hours. TFA was removed by distillation and the mixture was then purified according to the purification step A to give the title compound.
Yield amount: 6.6 mg
1H-NMR (D$_2$O) δ: 7.78-7.80 (m, 1H), 7.43-7.60 (m, 4H), 4.56-4.58 (m, 2H), 4.10-4.15 (m, 1H)
ESI-MS: 319 [M–H]$^-$, 321 [M+H]$^+$ Hereinafter, the synthesis of other representative compounds shown in TABLE 3 is described in more detail by referring to EXAMPLES. The compound of the present invention is not deemed to be limited by these EXAMPLES.

TABLE 3

| Ex. No. | Structure | 1H-NMR | MS (ESI, m/z) |
|---|---|---|---|
| 44 | 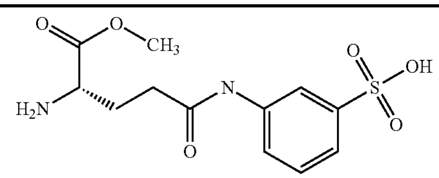 | 1H-NMR (DMSO-d6, 400 MHz): δ 10.1 (s, 1H), 8.39 (s, 3H), 7.83 (s, 1H), 7.59-7.58 (m, 1H), 7.38-7.21 (m, 2H), 4.12-4.11 (m, 1H), 3.75 (s, 3H), 2.46-2.44 (m, 2H), 2.12-2.08 (m, 2H) | 317 [M + H]$^+$ |
| 45 | 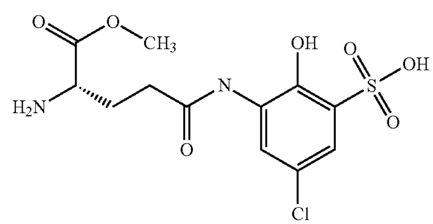 [SMILES: COC(=O)[C@@H](N)CCC(=O)Nc1cc(Cl)cc(S(=O)(=O)O)c1O] | 1H-NMR (DMSO-d6, 400 MHz) δ: 11.1 (s, 1H), 9.39 (s, 1H), 8.35 (s, 3H), 8.03 (s, 1H), 7.14 (s, 1H), 4.11-4.09 (m, 1H), 3.75 (s, 3H) 2.65-2.59 (m, 2H), 2.12-2.04 (m, 2H) | 367, 369 [M + H]$^+$ |
| 46 | 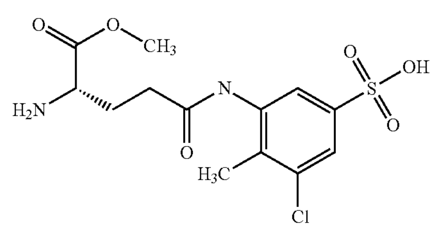 [SMILES: COC(=O)[C@@H](N)CCC(=O)Nc1cc(S(=O)(=O)O)cc(Cl)c1C] | 1H-NMR (DMSO-d6, 400 MHz) δ: 9.69 (s, 1H), 8.38 (s, 3H), 7.52 (s, 1H), 7.41 (s, 1H), 4.13-4.12 (m, 1H), 3.77 (s, 3H) 2.57-2.54 (m, 2H), 2.19 (s, 3H), 2.11-2.10 (m, 2H) | 365, 367 [M + H]$^+$ |

TABLE 3-continued

| Ex. No. | Structure | 1H-NMR | MS (ESI, m/z) |
|---|---|---|---|
| 47 | 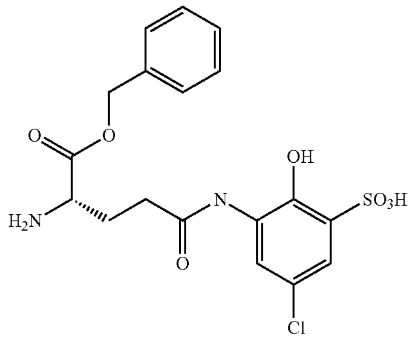 [SMILES: N[C@@H](CCC(=O)Nc1cc(Cl)cc(S(=O)(=O)O)c1O)C(=O)OCc1ccccc1] | | 443 [M + H]⁺ |
| 48 | 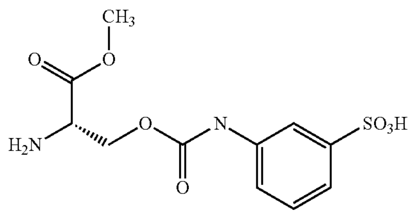 [SMILES: COC(=O)[C@@H](N)COC(=O)Nc1cccc(S(=O)(=O)O)c1] | 1H-NMR (D2O, 400 MHz) δ : 7.73 (s, 1H), 7.46 (m, 3H), 4.66 (dd, 1H), 4.58 (dd , 1H), 4.50 (dd, 1H), 3.82 (s, 3H) | 319 [M + H]⁺ |
| 49 | 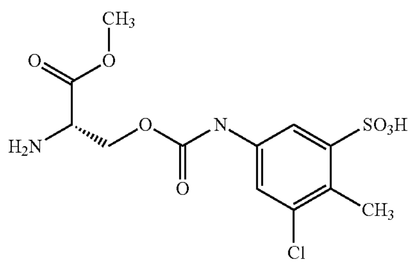 [SMILES: COC(=O)[C@@H](N)COC(=O)Nc1cc(Cl)c(C)c(S(=O)(=O)O)c1] | 1H-NMR (D2O, 400 MHz) δ : 7.40-7.72 (m, 2H), 4.47-4.67 (m, 3H), 3.82 (s, 3H), 2.52 (s, 3H) | 367, 369 [M + H]⁺ |
| 50 | 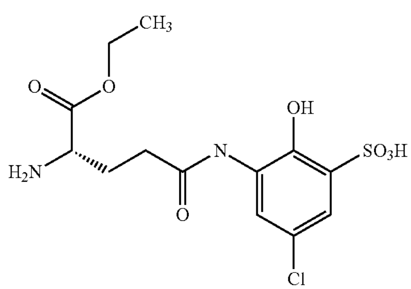 [SMILES: CCOC(=O)[C@@H](N)CCC(=O)Nc1cc(Cl)cc(S(=O)(=O)O)c1O] | 1H-NMR (DMSO-d6, 400 MHz) δ: 11.1 (s, 1H), 9.39 (s, 1H) 8.31 (s, 3H), 8.03 (s, 1H), 7.14 (s, 1H) 4.24-4.18 (m, 2H), 4.09-4.06 (m, 1H), 2.67-2.59 (m , 2H), 2.12-2.04 (m, 2H), 1.26-1.23 (m, 3H) | 381, 383 [M + H]⁺ |
| 51 | 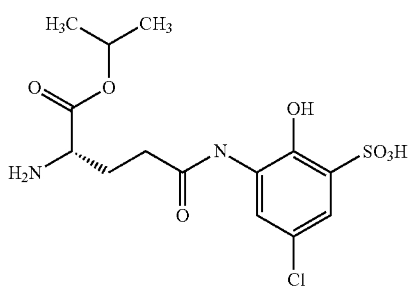 [SMILES: CC(C)OC(=O)[C@@H](N)CCC(=O)Nc1cc(Cl)cc(S(=O)(=O)O)c1O] | 1H-NMR (DMSO-d6, 400 MHz) δ: 11.0 (s, 1H), 9.34 (s, 1H), 8.24(s, 3H), 7.96 (s, 1H), 7.07 (s, 1 H), 4.97-4.91 (m, 1H), 3.98-3.97 (m, 1H) 2.57-2.52 (m, 2H), 2.03-1.96 (m, 2H), 1.20-1.18 (m, 6H) | 395, 397 [M + H]⁺ |

Synthesis Example 44

Synthesis of 3-[(4S)-4-amino-5-methoxy-5-oxopentanamido]benzene-1-sulfonic acid

Boc-Glu-OME, 130 mg (0.5 mmol), 190 mg (0.5 mmol) of 2-(7-azabenzotriazol-1-yl)-N,N,N',N'-tetramethyluronium hexafluorophosphate (HATU), 70 mg (0.5 mmol) of 7-aza-1-hydroxybenzotriazole (HOAt) and 87 mg (0.5 mmol) of 3-aminobenzenesulfonic acid were suspended in 2.0 ml of methylene chloride, and 0.5 ml of triethylamine was added to the suspension. The mixture was stirred at room temperature overnight. After the solvent was removed by distillation, the purification step A was applied to give the intermediate. The crude product was dissolved in 4.0 ml of trifluoroacetic acid (TFA) and stirred at room temperature for an hour. After the solvent was removed by distillation, the purification step A was applied to give 7.4 mg of the title compound.
Yield amount: 7.4 mg Synthesis Example 45

Synthesis of 3-[(4S)-4-amino-5-methoxy-5-oxopentanamido]-5-chloro-2-hydroxybenzene-1-sulfonic acid The title compound was obtained in the same way except that 3-amino-5-chloro-2-hydroxybenzenesulfonic acid was replaced for 3-aminobenzenesulfonic acid used in SYNTHESIS EXAMPLE 44.
Yield amount: 17.4 mg Synthesis Example 46

Synthesis of 3-[(4S)-4-amino-5-methoxy-5-oxopentanamido]-5-chloro-4-methylbenzene-1-sulfonic acid The title compound was obtained in the same way except that 3-amino-5-chloro-4-methylbenzenesulfonic acid was replaced for 3-aminobenzenesulfonic acid used in SYNTHESIS EXAMPLE 44.
Yield amount: 5.1 mg Synthesis Example 47

Synthesis of 3-[(4S)-4-amino-5-(benzyloxy)-5-oxopentanamido]-5-chloro-2-hydroxybenzene-1-sulfonic acid The title compound was obtained in the same way except that Boc-Glu-OBzl and 3-amino-5-chloro-2-hydroxybenzenesulfonic acid were replaced for Boc-Glu-OtBu and 3-sulfoaniline, respectively, used in SYNTHESIS EXAMPLE 44.

Synthesis Example 48

Synthesis of 3-({[(2S)-2-amino-3-methoxy-3-oxopropoxy]carbonyl}amino)benzene-1-sulfonic acid Boc-Ser-OME, 110 mg (0.5 mmol), and 87 mg (0.5 mmol) of 3-aminobenzenesulfonic acid were dissolved in 1 ml of pyridine, and 50 mg of triphosgene was added to the solution. The mixture was stirred at room temperature for 2 hours and the solvent was then distilled off. The resulting residue was purified according to the purification step A to give the crude product of the protected title compound. The crude product obtained was dissolved in 1 ml of methylene chloride and 1 ml of trifluoroacetic acid. The solution was stirred for 30 minutes at room temperature. After the solvent was distilled off, the mixture was purified in accordance with the purification step A to give the title compound.
Yield amount: 20.17 mg Synthesis Example 49

Synthesis of 5-({[(2S)-2-amino-3-methoxy-3-oxopropoxy]carbonyl}amino)-3-chloro-2-methylbenzene-1-sulfonic acid The title compound was obtained in the same way except that 5-amino-3-chloro-2-methylbenzenesulfonic acid was replaced for 3-aminobenzenesulfonic acid used in SYNTHESIS EXAMPLE 48.
Yield amount: 81.76 mg Synthesis Example 50

Synthesis of 3-[(4S)-4-amino-5-ethoxy-5-oxopentanamido]-5-chloro-2-hydroxybenzene-1-sulfonic acid Step 1

Synthesis of Boc-Glu-OEt 1.01 g (3.0 mmol) Boc-Glu (OBn)-OH, 1.01 g (3.0 mmol), 620 mg (3.1 mmol) of N,N-dicyclohexylamide (DCC) and 475 mg (3.1 mmol) of 1-hydroxybenzotriazole monohydrate (HOBt.H$_2$O) were suspended in 12 ml of methylene chloride. The suspension was cooled to 0° C. and 175 µl of ethyl alcohol was added thereto. After reverting to room temperature, stirring was continued overnight. The mixture was extracted with ethyl acetate/water. After the organic layer was washed with brine, sodium sulfate was added thereto and dried. The organic layer was concentrated under reduced pressure. The resulting residue was dissolved in 12 ml of methanol, and 100 mg of 10% Pd/C was added to the solution. The mixture was stirred in a hydrogen atmosphere overnight and the purification step A was applied to give the crude product of the title compound.
ESI (m/z): 276 [M+H]$^+$ Step 2

Synthesis of 3-[(4S)-4-amino-5-ethoxy-5-oxopentanamido]-5-chloro-2-hydroxybenzene-1-sulfonic acid After 92 mg (0.33 mmol) of the compound obtained in Step 1, 130 mg (0.33 mmol) of HATU, 45 mg (0.33 mmol) of HOAt and 77 mg (0.33 mmol) of 3-amino-5-chloro2-hydroxybenzenesulfonic acid were suspended in 1.0 ml of DMF, 0.25 ml of pyridine was added to the suspension. The mixture was stirred at room temperature overnight. The solvent was removed by distillation and the mixture was purified in accordance with the purification step A to give the intermediate. The crude product was dissolved in 4.0 ml of TFA. The solution was stirred at room temperature for an hour. The solvent was removed by distillation and the mixture was purified in accordance with the purification step A to give 47.2 mg of the title compound.
Yield amount: 47.2 mg Synthesis Example 51

Synthesis of 3-[(4S)-4-amino-5-oxo-5-(propan-2-yloxy)pentanamido]-5-chloro-2-hydroxybenzene-1-sulfonic acid The title compound was obtained in the same way except that 2-propanol was replaced for ethyl alcohol used in SYNTHESIS EXAMPLE 50.
Yield amount: 42.6 mg Example II Preparation of CaSR Gene The CaSR gene was prepared in accordance with the method described in Example 1 of WO 07/55393. Using the recombinant plasmid obtained, human CaSR expression plasmid hCaSR/pcDNA3.1 was prepared.

Example III

Evaluation of CaSR Agonist Activity (Evaluation of CaSR Agonist)

293E cells (HEK293 cells expressing EBNA1, ATCC No. CRL-10852) were cultured in DMEM (Dulbecco's Modified Eagle's Medium containing 1.0 g/ml glucose, NACALAI TESQUE, INC.) containing 10% fetal calf serum, in the presence of 250 µg/ml of G418. The cells were spread on a Petri dish of 10 cm diameter in $1.8 \times 10^6$ cells/15 ml. After the cells were allowed to stand in a $CO_2$ incubator (5% $CO_2$, 37° C.) for 24 hours, human CaSR expression plasmid hCaSR/pcDNA3.1 was transfected with a transfection reagent Mirus TransIT 293 (Takara Bio Inc.). After the cells were allowed to stand in the $CO_2$ incubator for 24 hours, the cells were collected by DMEM containing 10% fetal calf serum and plated on a poly-D-lysine coated 384 well plate (Falcon) in 15,000 cells/well. After the cells were allowed to stand in the $CO_2$ incubator for 24 hours, the medium was removed. Then, 50 µL/well of $Ca^{2+}$ fluorescence indicator Calcium 4 Assay Kit (Molecular Devices) that was dissolved in an assay buffer (146 mM NaCl, 5 mM KCl, 1 mM $MgSO_4$, 1 mg/ml glucose, 20 mM HEPES (pH 7.2) and 1.5 mM $CaCl_2$) was added thereto, and allowed to stand at 37° C. for an hour and then at room temperature for 30 minutes to load the fluorescence indicator. The 384 well plate described above was transferred to FLIPR (Molecular Devices), and 12.5 µL/well of a compound that was dissolved in a 0.1% BSA containing-assay buffer was added thereto. Changes in fluorescence intensity were monitored for 3 minutes. Compound No. 20 was purchased from Bachem.

(Method for Calculating $EC_{50}$)

The difference between the maximum and minimum fluorescent intensities (RFU (Max-Min) observed for each well before and after the addition of a test compound was determined by the automatic calculation using FLIPR. The activity rate was calculated based on the RFU (Max-Min) value observed when the maximum concentration of the compound added was defined as 100% and the RFU (Max-Min) value observed when the same concentration of DMSO added instead of the compound was defined as 0%. The resulting data was then input to the curve-fitting procedures using the spreadsheet software Xfit to determine the $EC_{50}$ that is a concentration of the compound at the activity rate of 50%. The results of the compounds of the present invention listed in TABLES 1 and 2 are shown in TABLES 4 and 5.

TABLE 4

| Compound No. | $EC_{50}$ [µM] |
|---|---|
| 1 | 0.012 |
| 2 | 2.3 |
| 3 | 0.56 |
| 4 | 0.059 |
| 5 | 0.13 |
| 6 | 2.7 |
| 7 | 0.0019 |
| 8 | 0.10 |
| 9 | 0.27 |
| 10 | 0.017 |
| 11 | 0.086 |
| 12 | 0.20 |
| 13 | 0.072 |
| 14 | 2.0 |

TABLE 4-continued

| Compound No. | $EC_{50}$ [µM] |
|---|---|
| 15 | 0.034 |
| 16 | 0.048 |
| 17 | 2.0 |
| 18 | 0.53 |
| 19 | 0.40 |
| 20 | 0.94 |

TABLE 5

| Compound No. | $EC_{50}$ [µM] |
|---|---|
| 21 | 0.0057 |
| 22 | 0.0014 |
| 23 | 0.89 |
| 24 | 0.022 |
| 25 | 0.97 |
| 26 | 0.16 |
| 27 | 0.15 |
| 28 | 0.33 |
| 29 | 0.53 |
| 30 | 2.9 |
| 31 | 3.7 |
| 32 | 0.0088 |
| 33 | 0.0021 |
| 34 | 0.0019 |
| 35 | 0.0037 |
| 36 | 3.5 |
| 37 | 0.0029 |
| 38 | 6.7 |
| 39 | 5.0 |
| 40 | 7.9 |
| 41 | 2.3 |
| 42 | 0.031 |
| 43 | 0.043 |

Example IV

Evaluation of CaSR Agonist Activity

The $EC_{50}$ values of Compound Nos. 44, 49 and 50 were measured in a manner similar to EXAMPLE III. The results are shown in TABLE 6.

TABLE 6

| Compound No. | $EC_{50}$ (µM) |
|---|---|
| 44 | 0.023 |
| 49 | 0.11 |
| 50 | 0.004 |

Example V

GLP-1 Secretion Promoting Activity

The following test was performed on Compound Nos. 1, 7, 21, 22, 33 and 34.

Human cecum-derived cell line NCI-H716 (ATCC No. CCL-251) was cultured in 10% FBS-containing DMEM/Ham's F-12 medium at 37° C. in the presence of 5% $CO_2$. The NCI-H716 cells were plated on a poly-D-lysine-coated 96-well plate in 100,000 cells/well, followed by culturing for 2 days. Prior to the addition of a sample, the wells were washed with Hepes buffer (20 mM Hepes, 146 mM NaCl, 5 mM KCl, 1.5 mM $CaCl_2$, 1 mM $MgSO_4$, 5.5 mM D-glucose, 0.2% BSA, pH 7.4). Then, 50 µl of a solution of the sample in the same buffer, and incubation was performed at 37° C. for 60 minutes. Compounds No. 1 (20 mM), No. 7 (20 mM), No. 21 (20 mM), No. 22 (20 mM), No. 33 (7.5 mM) and No. 34 (7.5 mM) listed in TABLE 1 were used as the sample. As for control, Hepes buffer was used. After the supernatant was collected, the cells were precipitated by centrifugation (5000×g, 1 minute) and the supernatant was recovered. The GLP-1 concentration in the supernatant was measured as follows by the method for GLP-1 quantification using the GLP-1 receptor gene expression cells.

Human GLP-1 receptor gene (SEQ ID NO: 1) was incorporated into pcDNA3.1 in a conventional manner (López de Maturana R, Willshaw A, Kuntzsch A, Rudolph R, Donnelly D. J. Biol. Chem. 2003 Mar. 21; 278 (12): 10195-200.) to construct human GLP-1 receptor gene expression plasmid hGLP-1R/pcDNA3.1. Also, the chimeric gene (SEQ ID NO: 2) of human Gα15 gene and human gustducin gene was incorporated into pcDNA3.1 to construct G-protein expression plasmid Gα15-gust/pcDNA3.1. Using a transfection reagent FuGene 6 (Roche Japan, Inc.), hGLP-1R/pcDNA3.1 and Gα15-gust44/pcDNA3.1 were cotransfected to HEK293E cells (ATCC No. CRL-10852). After incubation in a $CO_2$ incubator for 4 to 6 hours, the cells were suspended in 5% FBS-containing DMEM/Ham F12 and plated onto a poly-D-lysine-coated 96-well plate in 70,000 cells/well. After incubation for 24 hours in a $CO_2$ incubator, changes in fluorescence intensity were begun to monitor immediately after the addition of a sample, using a FlexStation (Molecular Devices) according to the $Ca^{2+}$ fluorescence indicator FLIPR Calcium 4 Assay Kit protocol (Molecular Devices). Concentration dependence in response to changes in fluorescence intensity of human GLP-1 (7-36 amide; Peptide Institute, Inc.) was determined and used as a standard curve for quantitative determination of the sample. The expression plasmid used here may be constructed by the methods described in, e.g., Proc. Natl. Acad. Sci. USA. 1992 Sep. 15; 89 (18): 8641-5, FEBS Letters Volume 373, Issue 29, October 1995, Pages 182-186), The Journal of Neuroscience, Aug. 13, 2003, 23 (19): 7376-7380), etc.

The results are shown in TABLE 7. The amount of GLP-1 secreted when the measurement value of control obtained using the buffer was made 1 was expressed as a relative value. The GLP-1 secretion promoting activity was confirmed in all of the compounds, indicating that the compounds of the present invention have the GLP-1 secretion promoting activity. Consequently, it was found that the compounds of the present invention are effective as the preventive or therapeutic agents for diabetes or obesity.

TABLE 7

| Compound No. | Relative Value |
| --- | --- |
| 1 | 1.82 |
| 7 | 2.90 |
| 21 | 4.38 |
| 22 | 2.22 |
| 33 | 1.87 |
| 34 | 2.88 |
| Buffer | 1.00 |

Example VI

CCK Secretion Promoting Activity

The following test was performed on Compound Nos. 1, 7, 21, 22, 33 and 34.

Human cecum-derived cell line NCI-H716 (ATCC No. CCL-251) was cultured in DMEM/Ham's F-12 medium containing 10% FBS at 37° C. in the presence of 5% $CO_2$. The NCI-H716 cells were plated on a poly-L-lysine-coated 24-well plate in 600,000 cells/well, followed by culturing for 2 days. Prior to the addition of a sample, the wells were washed with Hepes buffer (20 mM Hepes, 146 mM NaCl, 5 mM KCl, 1.5 mM $CaCl_2$, 1 mM $MgSO_4$, 5.5 mM D-glucose, 0.02% BSA, pH 7.4). Then, 300 μl of a solution of the sample in the same buffer, and incubation was performed at 37° C. for 30 minutes. Compounds No. 1 (20 mM) No. 7 (2 mM), No. 21 (2 mM), No. 22 (2 mM), No. 33 (0.1 mM) and No. 34 (1 mM) listed in TABLE 2 were used as the sample. For control, Hepes buffer was used. After the supernatant was collected, the cells were precipitated by centrifugation (5000×g, 1 minute). The supernatant was recovered and lyophilized in a SpeedVac Concentrator from Savant Instruments Inc., and 60 μl of water was added thereto for dissolution. The CCK concentration in the solution was determined using an Enzyme Immunoassay Kit (EK-069-04; PHOENIX PHARMACEUTICALS).

The results are shown in TABLE 8. The amount of CCK secreted when the measurement value of control obtained using the buffer was made 1 was expressed as a relative value. The CCK secretion promoting activity was confirmed in all of the compounds, indicating that the compounds of the present invention have the CCK secretion promoting activity. Therefore, it was also revealed from the CCK secretion promoting activity possessed by the compound of the present invention that the compounds of the present invention are effective as the preventive or therapeutic agents for diabetes or obesity.

TABLE 8

| Compound No. | Relative Value |
| --- | --- |
| 1 | 2.16 |
| 7 | 1.99 |
| 21 | 4.54 |
| 22 | 2.49 |
| 33 | 1.51 |
| 34 | 1.77 |
| Buffer | 1.00 |

Example VII

Gastric Emptying Suppression

After fasting for 24 hours, normal mice ((C57BL/6J, 7 weeks old) are forced to receive oral administration of an administration medium (distilled water) or the compound of the present invention using a sonde for mouse. For positive control, a group in which Exendin-4 (Sigma, Inc.) known to have a gastric emptying suppressing activity is subcutaneously injected in 2.4 nmol/kg may also be used as a positive group. Each mouse in the Exendin-4 group is also orally given the administration medium in 10 ml/kg. Fifteen minutes after the drug administration, the mouse is received phenol red solution (0.5 mg/ml phenol red+1.5% methylcellulose+distilled water) by forced administration in 5 ml/kg. The stomach is removed 20 minutes later, and phenol red remained in the stomach is extracted in 0.1N NaOH solution. Absorbance of the solution extracted is measured at 560 nm to quantitatively determine the amount (S) of phenol red remained. When the amount (C) of phenol red extracted from the stomach removed immediately after administration of phenol red is made 100%, the gastric emptying is determined by calculating the ratio of phenol red remained 20 minutes after drug administration to C based on the following calculation formula.

Gastric emptying(%)=(1−(S/C))×100

According to the method above, it can be confirmed that the compound of the present invention has the gastric emptying suppressing activity. Therefore, it can be confirmed that the compound of the present invention has the food intake suppressing activity and the antiobesity activity.

Example VIII

Suppression of Blood Glucose Increase

After preliminary rearing (7 days), male mice (C57BL/6J, 7 weeks old) are fasted overnight and underwent an oral glucose loading test as follows. The animal is given a glucose solution only (2 g/kg body weight) and a glucose solution containing the compound of the present invention (2 g/kg body weight). Blood is collected from the tail vein 15, 30, 60, 120 and 180 minutes after administration of a sample, and the glucose level in plasma is determined using a commercially available kit (Roche).

It can be confirmed by this method that the compound of the present invention has the activity of suppressing blood glucose increase.

INDUSTRIAL APPLICABILITY

The compound of the present invention or salts thereof, as well as drugs thereof exhibit the excellent CaSR agonist activity and further exhibit the GLP-1 secretion promoting activity and the CCK secretion promoting activity, and are useful as the preventive or therapeutic agents for diseases that can be treated by these activities, especially diabetes or obesity, and so on.

CROSS-REFERENCES TO RELATED APPLICATIONS

This application is a continuation of International Patent Application No. PCT/JP2011/058855, filed on Mar. 31, 2011, and claims priority to Japanese Patent Application No. 2010-085741, filed on Apr. 2, 2010, both of which are incorporated herein by reference in their entireties.

The invention claimed is:

1. A method for treating diabetes or obesity, comprising:
administering to a subject in need thereof, an effective amount of a glutamic acid compound represented by formula (I):

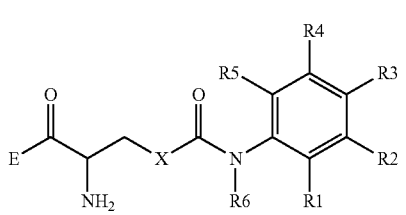

wherein $R^1$, $R^2$, $R^3$, $R^4$ and $R^5$ each independently is selected from the group consisting of a hydrogen atom, a halogeno group, a hydroxyl group, a nitro group, an amino group, a $C_{1-6}$ alkyl group which may have a substituent(s), a $C_{1-6}$ alkoxy group which may have a substituent(s), a $C_{1-6}$ mono- or dialkylamino group which may have a substituent(s), a sulfo group, and a group:

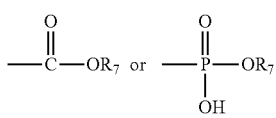

provided that either one of $R^1$, $R^2$ and $R^3$ is selected from the group consisting of a nitro group, a sulfo group and a group:

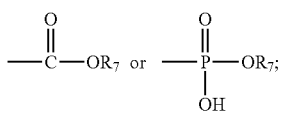

$R^6$ is a hydrogen atom, a hydroxyl group or a $C_{1-6}$ alkyl group which may have a substituent(s);
$R^7$ is a hydrogen atom or a $C_{1-6}$ alkyl group which may have a substituent(s);
X is a methylene group or an oxygen atom; and,
E is a hydroxyl group, a $C_{1-6}$ alkoxy group which may have a substituent(s), a mercapto group which may have a substituent(s), or a group:

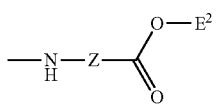

wherein Z is selected from the group consisting of a divalent $C_{1-6}$ hydrocarbon group which may have a substituent(s), and $E^2$ is a hydrogen atom or a $C_{1-6}$ alkyl group;
or a pharmaceutically acceptable salt thereof.

2. A method according to claim 1, wherein, in formula (I):
$R^1$, $R^2$, $R^3$, $R^4$ and $R^5$ each independently is selected from the group consisting of a hydrogen atom, a halogeno group, a hydroxyl group, a nitro group, an amino group, a $C_{1-6}$ alkyl group which may have a substituent(s), a $C_{1-6}$ alkoxy group which may have a substituent(s), and a $C_{1-6}$ mono- or dialkylamino group which may have a substituent(s);
$R^2$ is selected from the group consisting of a nitro group, a sulfo group and a group:

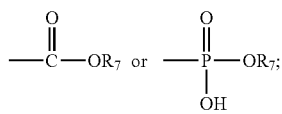

$R^6$ and $R^7$ each independently is a hydrogen atom or a $C_{1-6}$ alkyl group which may have a substituent(s); and,
X is a methylene group or an oxygen atom.

3. A method according to claim 1, wherein, in formula (I):
$R^1$, $R^3$, $R^4$ and $R^5$ each independently is selected from the group consisting of a hydrogen atom, a halogeno group, a hydroxyl group, a nitro group, an amino group, a $C_{1-3}$ alkyl group which may have a substituent(s), a $C_{1-3}$ alkoxy group which may have a substituent(s) and a $C_{1-3}$ mono- or dialkylamino group which may have a substituent(s);
$R^2$ is selected from the group consisting of a nitro group, a sulfo group, and a group:

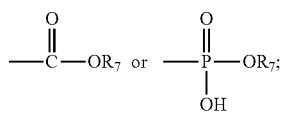

and,
$R^6$ and $R^7$ each independently is a hydrogen atom or a methyl group.

4. A method according to claim 1, wherein, in formula (I):
$R^1$, $R^3$, $R^4$ and $R^5$ each independently is selected from the group consisting of a hydrogen atom, a chloro or bromo group, a hydroxyl group, a nitro group, an amino group, a methyl group and a methoxy group;
$R^2$ is selected from the group consisting of a nitro group, a sulfo group and a group:

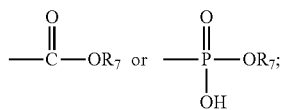

$R^6$ is a hydrogen atom or a methyl group;
$R^7$ is a hydrogen atom; and,
X is a methylene group.

5. A method according to claim 1, wherein, in formula (I):
$R^2$ is a sulfo group, a carboxylic acid group or a phosphonic acid group.

6. A method according to claim 1, wherein, in formula (I):
E is a hydroxyl group or a $C_{1-6}$ alkoxy group which may have a substituent(s).

7. A method according to claim 1, wherein, in formula (I):
E is a $C_{1-6}$ alkoxy group or a group:

$$-O-Z-E^1 \quad \text{(IIa)}$$

wherein, in formula (IIa):
Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), a carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), and Z and $E^1$ may be combined together to form a ring.

8. A method according to claim 1, wherein the glutamic acid compound is administered in an amount of 0.000001% by weight to 99.9999% by weight based on a dry weight.

9. A method according to claim 1, wherein the glutamic acid compound is administered in an amount of 0.00001% by weight to 99.999% by weight based on a dry weight.

10. A method according to claim 1, wherein the glutamic acid compound is administered in an amount of 0.0001% by weight to 99.99% by weight based on a dry weight.

* * * * *

SEQUENCE LISTING

```
<160> NUMBER OF SEQ ID NOS: 2

<210> SEQ ID NO 1
<211> LENGTH: 1441
<212> TYPE: DNA
<213> ORGANISM: Homo sapiens

<400> SEQUENCE: 1
ccgcggccgc cccttcacc  tgaactcccc gccatggccg gcgccccgg  cccgctgcgc       60 cttgcgctgc tgctgctcgg gatggtgggc agggccggcc cccgccccca gggtgccact      120
gtgtccctct gggagacggt gcagaaatgg cgagaatacc gacgccagtg ccagcgctcc      180
ctgactgagg atccacctcc tgccacagac ttgttctgca accggacctt cgatgaatac      240
gcctgctggc cagatgggga gccaggctcg ttcgtgaatg tcagctgccc ctggtacctg      300
ccctgggcca gcagtgtgcc gcagggccac gtgtaccggt tctgcacagc tgaaggcctc      360
tggctgcaga aggacaactc cagcctgccc tggagggact tgtcggagtg cgaggagtcc      420
aagcgagggg agagaagctc cccggaggag cagctcctgt tcctctacat catctacacg      480
gtgggctacg cactctcctt ctctgctctg gttatcgcct ctgcgatcct cctcggcttc      540
agacacctgc actgcacccg gaactacatc cacctgaacc tgtttgcatc cttcatcctg      600
cgagcattgt ccgtcttcat caaggacgca gccctgaagt ggatgtatag cacagccgcc      660
cagcagcacc agtgggatgg gctcctctcc taccaggact ctctgagctg ccgcctggtg      720
tttctgctca tgcagtactg tgtggcggcc aattactact ggctcttggt ggagggcgtg      780
tacctgtaca cactgctggc cttctcggtc ttctctgagc aatggatctt caggctctac      840
gtgagcatag gctggggtgt tccctgctg tttgttgtcc cctggggcat tgtcaagtac      900
ctctatgagg acgagggctg ctggaccagg aactccaaca tgaactactg gctcattatc      960
cggctgccca ttctctttgc cattgggggtg aacttcctca tctttgttcg ggtcatctgc     1020
atcgtggtat ccaaactgaa ggccaatctc atgtgcaaga cagacatcaa atgcagactt     1080
```

-continued

| | |
|---|---|
| gccaagtcca cgctgacact catcccctg ctggggactc atgaggtcat ctttgccttt | 1140 |
| gtgatggacg agcacgcccg ggggaccctg cgcttcatca agctgtttac agagctctcc | 1200 |
| ttcacctcct tccaggggct gatggtggcc atcttatact gctttgtcaa caatgaggtc | 1260 |
| cagctggaat tcggaagag ctgggagcgc tggcggcttg agcacttgca catccagagg | 1320 |
| gacagcagca tgaagcccct caagtgtccc accagcagcc tgagcagtgg agccacggcg | 1380 |
| ggcagcagca tgtacacagc cacttgccag gcctcctgca gctgaaaggg tgggcgcgcc | 1440 |
| g | 1441 |

<210> SEQ ID NO 2
<211> LENGTH: 1125
<212> TYPE: DNA
<213> ORGANISM: Artificial Sequence
<220> FEATURE:
<223> OTHER INFORMATION: chimeric gene of human Galpha 15 and Gastducin

<400> SEQUENCE: 2

| | |
|---|---|
| atggcccgct cgctgacctg gcgctgctgc ccctggtgcc tgacggagga tgagaaggcc | 60 |
| gccgcccggg tggaccagga gatcaacagg atcctcttgg agcagaagaa gcaggaccgc | 120 |
| ggggagctga agctgctgct tttgggccca ggcgagagcg ggaagagcac cttcatcaag | 180 |
| cagatgcgga tcatccacgg cgccggctac tcggaggagg agcgcaaggg cttccggccc | 240 |
| ctggtctacc agaacatctt cgtgtccatg cgggccatga tcgaggccat ggagcggctg | 300 |
| cagattccat tcagcaggcc cgagagcaag caccacgcta gcctggtcat gagccaggac | 360 |
| ccctataaag tgaccacgtt tgagaagcgc tacgctgcgg ccatgcagtg gctgtggagg | 420 |
| gatgccggca tccgggcctg ctatgagcgt cggcgggaat ccacctgct cgattcagcc | 480 |
| gtgtactacc tgtcccacct ggggcgcatc accgaggagg gctacgtccc cacagctcag | 540 |
| gacgtgctcc gcagccgcat gcccaccact ggcatcaacg agtactgctt ctccgtgcag | 600 |
| aaaaccaacc tgcggatcgt ggacgtcggg ggccagaagt cagagcgtaa gaaatggatc | 660 |
| cattgtttcg agaacgtgat cgccctcatc tacctagcct cactgagtga atacgaccag | 720 |
| tgcctggagg agaacaacca ggagaaccgc atgaaggaga gcctcgcatt gtttgggact | 780 |
| atcctggaac tacctggtt caaaagcaca tccgtcatcc tctttctcaa caaaaccgac | 840 |
| atcctggagg agaaaatccc cacctcccac ctggctacct atttccccag tttccagggc | 900 |
| cctaagcagg atgctgaggc agccaagagg ttcatcctgg acatgtacac gaggatgtac | 960 |
| accgggtgcg tggatggccc cgagggcagc aatttaaaaa agaagataaa ggaaatttat | 1020 |
| tcccacatga cctgtgctac tgacacccaa aatgtcaagt tgtgtttga cgcagttaca | 1080 |
| gatataataa tcaaagagaa tctaaaagac tgtgggcttt ctaa | 1125 |